United States Patent [19]
Heise

[11] Patent Number: 6,090,950
[45] Date of Patent: Jul. 18, 2000

[54] CHIRAL HYDRIDE COMPLEXES

[75] Inventor: Glenn L. Heise, Grand Haven, Mich.

[73] Assignee: Zeeland Chemicals, Inc., Zeeland, Mich.

[21] Appl. No.: 08/709,191

[22] Filed: Aug. 23, 1996

[51] Int. Cl.$^7$ ............................................... C07D 305/00
[52] U.S. Cl. ......................... 549/210; 536/17.1; 546/6; 546/13; 548/403; 548/405; 549/213; 556/181; 556/182; 556/183; 556/176; 558/287; 560/180; 564/9; 564/160; 568/6; 568/814
[58] Field of Search .................... 423/644, 646; 252/188.26, 188.27; 549/210

[56] References Cited

U.S. PATENT DOCUMENTS

| | | | |
|---|---|---|---|
| 3,619,370 | 11/1971 | Weinstock et al. | 195/51 |
| 3,704,249 | 11/1972 | Czaja et al. | 260/343.2 |
| 3,852,262 | 12/1974 | Vit et al. | 260/205 |
| 4,059,585 | 11/1977 | Bruderlein | 260/286 |
| 4,147,530 | 4/1979 | Langer, Jr. et al. | 75/5 A |
| 4,284,581 | 8/1981 | Noyori | 260/448 |
| 4,328,164 | 5/1982 | Bergman et al. | 260/439 |
| 4,376,217 | 3/1983 | Bergman et al. | 564/448 |
| 4,603,213 | 7/1986 | Hajos | 549/363 |
| 4,665,207 | 5/1987 | Marlett | 556/176 |
| 4,701,540 | 10/1987 | Lukac et al. | 549/341 |
| 4,739,082 | 4/1988 | Noe et al. | 549/386 |
| 5,210,243 | 5/1993 | Kolich | 556/18 |
| 5,231,227 | 7/1993 | Yoneyoshi et al. | 564/390 |
| 5,266,723 | 11/1993 | Hanna et al. | 562/490 |
| 5,288,918 | 2/1994 | Maher et al. | 563/454 |
| 5,292,893 | 3/1994 | Buchwald et al. | 548/577 |
| 5,648,541 | 7/1997 | VanWagenen | 564/375 |

FOREIGN PATENT DOCUMENTS

| | | |
|---|---|---|
| 0204340 | 12/1986 | European Pat. Off. . |
| 0353053 | 1/1990 | European Pat. Off. . |
| 0457559 | 11/1991 | European Pat. Off. . |
| 0471498 | 2/1992 | European Pat. Off. . |
| 2259823 | 8/1975 | France . |
| 2414188 | 11/1974 | Germany . |
| 2940336 | 4/1980 | Germany . |
| 60-16982 | of 1985 | Japan . |
| 1-199958 | of 1989 | Japan . |
| 2188633 | 10/1987 | United Kingdom . |
| WO 97/13763 | 4/1997 | WIPO . |

OTHER PUBLICATIONS

Bothner–By, J. Am. Chem. Soc. 73:846–847 (1951).
Adolph et al., Cell 12:805–816 (1977).
Alcaide et al., Anales De Quimica 82:168–169 (1986).
Altman et al., Tetrahedron Letters 29:2493–2496 (1976).
ApSimon et al., Tetrahedron 42:5157–5254 (1986).
Asami et al., Bulletin of the Chemical Society of Japan 51(6):1869–1873 (1978).
Blaser, Chem Rev. 92:935–952 (1992).
Brown et al., Tetrahedron Asymetry 2:339–342 (1991).
Brown et al., J. Org. Chem. 52:5406–5412 (1987).
Cervinka et al., Collect. Czech. Chem. Commun. 32:3897–3908 (1967).
Cervinka et al., Tetrahedron Letters 13:1179–1180 (1967).
Cervinka, Collect. Czech. Chem. Commun. 30:1684–1691 (1965).
Cervinka, Collect. Czech. Chem. Commun. 30:2403–2409 (1965).
Cervinka, Collect. Czech. Chem. Commun. 30:2487–2491 (1965).
Cha et al., J. Org. Chem. 58:4727–4731 (1993).
Cohen et al., J. Org. Chem. 45:582–588 (1980).
Dale et al., J. Org. Chem. 34:2543–2549 (1969).
Evans et al., Tetrahedron Letters 21:4233–4236 (1980).
Frechet et al., J. Org. Chem. 51:3462–3467 (1986).
Garry et al., J. Chem. Soc. Perkin Trans I 601–605 (1987).
Giordano et al., J. Org. Chem. 54:1470–1473 (1989).
Haubenstock et al., J. Org. Chem. 84:2363–2368 (1962).
Harashima et al., Tetrahedron 147:2773–2784 (1991).
Hill et al., Org. Syn. Coll. vol. VII:461–467.
Ibarra et al., J. Chem. Soc. Perkin Trans. II pp. 101–105 (1988).
Itsuno et al., J. Chem. Soc. Perkin Trans. I pp. 2887–2893 (1984).
Itsuno et al., J. Chem. Soc. Soc. Chem. Commun. pp. 467–470 (1983).
Koreeda et al., Tetrahedron Letters 50:4565–4568 (1976).
Kyba et al., J. Org. Chem. 42:4173–4184 (1977).
Landor et al., Bull. Chem. Soc. Jpn. 57:1658–1661 (1984).
Landor et al., J. Chem. Soc. Perkin Trans. I pp. 493–496 (1984).

(List continued on next page.)

*Primary Examiner*—Michael L. Shippen
*Attorney, Agent, or Firm*—Pennie & Edmonds LLP

[57] ABSTRACT

Novel chiral boron and aluminum hydride complexes, compositions comprising the chiral hydride complexes, and methods for their synthesis and use are described. The novel chiral hydride complexes are of the formulas:

$MBH_{4-n-a}(R^*)_n(R')_a$;
$MBH_{2-b}(R^{**})(R')_b$;
$MBH(R^{***})$;
$MBH(R^*)(R'')$;
$MAlH_{4-n-a}(R^*)_n(R')_a$;
$MAlH_{2-b}(R^{**})(R')_b$;
$MAlH(R^{***})$; and
$MAlH(R^*)(R'')$, wherein M is $Na^+$, $Li^+$ or $K^+$;
each $R^*$ is independently a monodentate chiral ligand;
$R^{**}$ is a bidentate chiral ligand;
$R^{***}$ is a tridentate chiral ligand;
$R'$ is a monodentate achiral ligand;
$R''$ is a bidentate achiral ligand;
n is 1–3;
a is 0–2; and
b is 0–1, with the proviso that $n+a \leq 3$, and with the further proviso that when $R^{**}$ is S-BINOL, M is not $Li^+$.

2 Claims, No Drawings

OTHER PUBLICATIONS

Landor et al., J. Chem. Soc. Perkin Trans. I pp. 1902–1903 (1974).
Landor et al., J. Chem. Soc. (C) pp. 2339–2341 (1971).
Landor et al., J. Chem. Soc. (C) pp. 197–201 (1967).
Landor et al., J. Chem. Soc. Commun. pp. 585–586 (1966).
Landor et al., J. Chem. Soc. (C) pp. 1822–1825 (1966).
Landor et al., J. Chem. Soc. (C) pp. 2280–2282 (1966).
Lund et al., J. Org. Chem. 12:2073–2076 (1977).
Mash et al., Org. Syn. 68:92–103 (1989).
Meyer et al., Liebigs Ann. Chem. pp. 2261–2278 (1975).
Meyers et al., Tetrahedron Letters 14:1337–1340 (1974).
Miyashita et al., Tetrahedron 40:1245–1253 (1984).
Minoura et al., J. Polymer Sci.:Part A–1 6:2013–2021 (1968).
Mori et al., Tetrahedron 39:2303–2306 (1983).
Mukaiyama and Asami, "Chiral Pyrrolidine Diamines as Efficient Ligands in Asymetric Synthesis" pp. 134–167.
Noyori et al., J. Am. Chem. Soc. 106:6709–6716 (1984).
Noyori et al., J. Am. Chem. Soc. 106:6717–6725 (1984).
Noyori et al., J. Am. Chem. Soc. 101:5843–5844 (1979).
Noyori et al., J. Am. Chem. Soc. 101:3129–3131 (1979).
Oishi et al., Tetrahedron Letters 33:639–642 (1992).
Ookawa et al., J. Chem. Perkin Trans. I pp. 1465–1471 (1987).
Pohland et al., J. Am. Chem. Soc. 75:4458–4461 (1953).
Portoghese, J. Org. Chem. 27:3359–3360 (1962).
Rao et al., J. Chem. Soc. Chem/ Commun. pp. 1273–1274 (1988).
Saigo et al., Chemistry Letters pp. 545–548 (1979).
Sandman et al., J. Am. Chem. Soc. 90:4877–4884 (1968).
Sato et al., Tetrahedron Letters 24:4123–4126 (1983).
Schmidt et al., Chem. Ber. 113:1691–1707 (1980).
Schubert et al., Tetrahedron 39:2211–2217 (1983).
Schultz et al., Tetrahedron Letters 26:4575–4578 (1985).
Shing et al., J. Chem. Soc. Chem. Commun. pp. 262–263 (1987).
Suda et al., Chemistry Letters pp. 899–902 (1984).
Suda et al., Tetrahedron Letters 24:1513–1516 (1983).
Suda et al., Tetrahedron Letters 47:4565–4568 (1979).
Tani et al., J. Chem. Soc. Commun. pp. 600–601 (1982).
Toda et al., Tetrahedron Letters 29:551–554 (1988).
Tomioka, Synthesis pp. 541–549 (Jul. 1990).
Trost et al., J. Am. Chem. Soc. 109:1469–1478 (1987).
Valcavi et al., Annali Di Chimica 65:91–98 (1975).
Vigneron et al., Tetrahedron 32939–944 (1976).
Yamaguchi et al., J. Am. Chem. Soc. 94:9254–9255 (1972).
ter Halle, Rob et al.; "Chiral Nitrogen–Metal Complexes for the Asymmetric Reduction of Ketones"; Tetrahedron:Asymmetry, vol. 8, No. 13, Jul. 10, 1997, pp. 2101–2108.
Landor, J. Chem. Soc. (C), pp. 1822–1825, 1966.
Seebach et al., Croat. Acta (1996), 69(2), 459–484, 1996.

CHIRAL HYDRIDE COMPLEXES

FIELD OF THE INVENTION

The present invention relates to novel chiral hydride complexes useful as reducing agents for chemical entities bearing carbonyl groups or their equivalents, compositions comprising the chiral hydride complexes, and methods for their synthesis and use.

BACKGROUND OF THE INVENTION

In recent years there has been intensive investigations to further the cause of asymmetric reduction specifically as it relates to the development of new pharmaceutical intermediates and bulk drugs. This effort has been spurred by the benefits of single isomer or enantiopure compounds used as pharmaceutical drug agents. Factors such as availability and the overall economics and safety related to the use of new reagents has promoted the idea that an ideal chiral reducing agent could be fabricated from cost effective precursors with the chiral moiety being derived from readily available members of the chiral pool.

Among the techniques for introducing chirality that are available to the industrial chemist, the one that has proven especially useful is asymmetric reduction. Reduction of unsymmetrical ketones to alcohols is among the most useful. This reaction is achieved by the overall addition of hydride ("H—") to one face of the carbonyl group leading preferentially to the formation of one enantiomer.

It is known in the art that several lithium-based chiral reagents have been synthesized via selective substitution of 1–3 hydrogen atoms of lithium aluminum hydride ("LAH") by protic chiral ligands. Early attempts (A. A. Bothner-By, J. Am. Chem. Soc. 73, 846 (1951)) focused on the reaction of LAH with camphor to produce a reagent consisting of LAH complexed with one equivalent of (+)-isoborneol. This reagent was used to reduce prochiral ketones like methyl ethyl ketone or methyl-t-butyl ketone to produce optically active carbinols. These results were later challenged (P. S. Portoghese, J. Org. Chem. 27, 3359 (1962)) by suggesting that the alcohols obtained by Bothner-By were actually achiral and contaminated with small amounts of (+)-borneol. The failure to induce chirality in simple ketones upon reduction with a reagent utilizing LAH and chiral auxiliaries (−)menthol and (+)borneol was later reported (O. Cervinka, Collect. Czech. Chem. Commun. 30, 1684 (1965); O. Cervinka, Collect. Czech. Chem. Commun. 30, 2403 (1965)). Cervinka was able to demonstrate in later papers that the reduction of pyrrolinium salts and ketamines using LAH modified with chiral terpenoids, such as (+)-borneol, (+)-camphor, (−)-menthol and (+)-homopherehyl alcohol, resulted in the corresponding amines having low optical purity, indicating that only partial enantioselectivity had been achieved.

In 1967, monohydroxy sugar derivatives as well as chiral phenylmethyl- and t-butylcarbinols were used as LAH modifiers in the reductions of simple prochiral ketones with only modest success (O. Cervinka et al., Tetrahedron Lett., 1179 (1967)). While (+)-camphor-modified LAH induced chirality in reduction of methyl ethyl ketone, the resulting enantiomeric excess was only 2% (Y. Minoura et al., J. Polym. Sci. Part A-1 6, 2013 (1968)). Other investigators have reported that successful asymmetric reduction of alpha and beta-dialkylamino ketones could be obtained using LAH modified with three equivalents of (−)-menthol in up to 95% enantiomeric excess (R. Andrisano et al., Tetrahedron, 913 (1973); A. S. Angeloni et al., Gazz. Chim. Ital. 107, 421 (1977)). Some of these results have been unable to be reproduced (S. Yamaguchi et al., Bull. Chem. Soc. Jpn. 50, 3033 (1977).

The use of glucose derivatives as LAH modifiers in the reduction of various substrates has also been reported, although with generally low optical yields (S. R. Landor et al., J. Chem. Soc. Chem. Commun., 585 (1966); S. R. Landor et al., J. Chem. Soc. Chem. Commun., 1822 (1966); S. R. Landor et al., J. Chem. Soc. C, 2339 (1971); S. R. Landor et al., J. Chem. Soc. Perkin Trans. 1, 1902 (1974). S. R. Landor et al., J. Chem. Soc. Perkin Trans. 1, p. 605 (1974). Mannitol derivatives which had a C2 axis of symmetry have been used as LAH modifiers, but the values of enantiomeric excess obtained in the resulting products were less than 15% (N. Baggett et al., J. Chem. Soc. Perkin Trans. I, 1123 (1977).

The most efficient chiral auxiliary reported to modify LAH was binaphthol ("BINOL"). Use of BINOL and an achiral auxiliary like ethanol as a ligand for LAH has been reported to result in a reagent that reduces several ketones with high enantiomeric excess (e.e.) (>99%) (R. Noyori et al., J. Am. Chem. Soc. 101, 3129 (1979); R. Noyori et al., J. Am. Chem. Soc. 101, 5843 (1979)). However, commercial interest in binaphthol as a stoichiometric reducing agent has been limited due to its extremely high initial cost, complicated synthesis and difficult recovery from a reduction reaction.

Another report has stated that 1,2-amino alcohols and several diamines have been able to impart some asymmetry to hydride reducing agents (M. Asami, and T. Mukaiyama, Heterocycles 12, 499 (1979)).

To the knowledge of the inventors, prior studies have not demonstrated the utility of inexpensive, readily available chiral auxiliaries in boron or aluminum hydride reducing agents, with or without the use of achiral auxiliaries, to impart significant enantioselectivities when reacted with prochiral ketones.

Thus, there is a need for new chiral hydride reducing agents which can be readily derived from inexpensive sources or easily synthesized, and which are capable of enantioselectively delivering a source of hydride to carbonyl or carbonyl-equivalent bearing chemical entities to afford reduction products in good yield and with high enantioselectivity.

SUMMARY OF THE INVENTION

The present invention provides novel chiral boron or aluminum hydride complexes having the structures of the general formulas:

$MBH_{4-n-a}(R^*)_n(R')_a$;

$MBH_{2-b}(R^{**})(R')_b$;

$MBH(R^{***})$;

$MBH(R^*)(R'')$;

$MAlH_{4-n-a}(R^*)_n(R')_a$;

$MAlH_{2-b}(R^{**})(R')_b$;

$MAlH(R^{***})$; and $MAlH(R^*)(R'')$, wherein

M is $Na^+$, $Li^+$ or $K^+$;

each R* is independently a monodentate chiral ligand derived from optionally protected carbohydrates, amino acids, amino alcohols, alkaloids, chiral aromatic or alkyl alcohols, chiral aromatic or alkyl amines or combinations thereof;

R** is a bidentate chiral ligand derived from optionally protected carbohydrates, amino acids, amino alcohols, alkaloids, chiral aromatic or alkyl alcohols, chiral aromatic or alkyl amines, chiral diamines, chiral diols, chiral biaryl alcohols, chiral biaryl amines, D- or L-tartaric acid or combinations thereof;

R*** is a tridentate chiral ligand derived from optionally protected carbohydrates, amino acids, amino alcohols, alkaloids, chiral aromatic or alkyl alcohols, chiral aromatic or alkyl amines or combinations thereof;

R' is a monodentate achiral ligand selected from the group consisting of alkylalcohols, arylalcohols, arylalkyl alcohols, alkylamines, arylamines, arylalkyl amines, alkylthiols, arylthiols, arylalkyl thiols and, in the case of $MBH_{4-n-a}(R^*)_n(R')_a$, and $MBH_{2-b}(R^{**})(R')_b$, R' may also be cyanide;

R" is a bidentate achiral ligand selected from the group consisting of alkyldiols, aryldiols, arylalkyl diols, alkyldiamines, aryldiamines, arylalkyl diamines, alkyldithiols, arylthiols, arylalkyl thiols, mercaptoalcohols, mercaptoamines, and aminoalcohols;

n is 1–3;
a is 0–2; and
b is 0–1, with the proviso that n+a≦3, and with the further proviso that when R** is S-BINOL, M is not Li+. These complexes are useful as enantioselective hydride reducing agents for carbonyl groups and carbonyl equivalents.

The invention also encompasses certain novel chiral ligands which are used for synthesizing these complexes.

In these methods, the novel chiral hydride complexes are synthesized by admixing in the presence of an organic solvent 1 equivalent of $MAlH_4$ or $MBH_4$ with 1 to 3 equivalents of R*, and optionally with 1–2 equivalents of R', such that the total equivalents of R* and R' relative to $MAlH_4$ or $MBH_4$ does not exceed three; with 1 equivalent of R* and optionally with 1 equivalent of R"; with 1 equivalent of R, and optionally with 1 equivalent of R'; or with 1 equivalent of R*.

The invention further provides methods for synthesizing the novel chiral complexes comprising admixing in the presence of an organic solvent 1 equivalent of $MBH_3(CN)$ with 1–2 equivalents of R* and optionally with 1 equivalent of R', such that the total equivalents of R* and R' relative to $MBH_3(CN)$ does not exceed two; or with 1 equivalent of R**.

The invention still further provides compositions useful for enantioselectively reducing a chemical entity having a carbonyl group or a carbonyl equivalent, the compositions being obtained by the previous methods. Such compositions optionally contain other agents useful for imparting enantioselectivity to carbonyl group and carbonyl equivalent-containing substrates.

Still further, the invention provides methods for obtaining an enantiomeric excess of a reduction product comprising enantioselectively reducing a carbonyl group or carbonyl equivalent of a chemical entity by admixing the chemical entity with the chiral hydride complex of the present invention, or with a composition that includes such complexes.

Further still, the invention provides chiral hydride reducing agents comprising a solid phase support.

The present invention may be understood more fully by reference to the following detailed description and illustrative examples which are intended to exemplify non-limiting embodiments of the invention.

DETAILED DESCRIPTION OF THE INVENTION SYNTHESIS OF THE CHIRAL HYDRIDE COMPLEXES

The chiral boron or aluminum hydride complexes of the present invention are represented by the general formulas:

$MBH_{4-n-a}(R^*)_n(R')_a$;
$MBH_{2-b}(R^{**}) (R')_b$;
$MBH(R^{***})$;
$MBH(R^*) (R")$;
$MAlH_{4-n-a}(R^*)_n(R')_a$;
$MAlH_{2-b}(R^{**})(R')_b$;
$MAlH(R^{***})$; and
$MAlH(R^*)(R")$, wherein:

M is Na+, Li+ or K+;

each R* is independently a monodentate chiral ligand derived from optionally protected carbohydrates, amino acids, amino alcohols, alkaloids, chiral aromatic or alkyl alcohols, chiral aromatic or alkyl amines or combinations thereof;

R** is a bidentate chiral ligand derived from optionally protected carbohydrates, amino acids, amino alcohols, alkaloids, chiral aromatic or alkyl alcohols, chiral aromatic or alkyl amines, chiral diamines, chiral diols, chiral biaryl alcohols, chiral biaryl amines, D- or L-tartaric acid or combinations thereof;

R*** is a tridentate chiral ligand derived from optionally protected carbohydrates, amino acids, amino alcohols, alkaloids, chiral aromatic or alkyl alcohols, chiral aromatic or alkyl amines or combinations thereof;

R' is a monodentate achiral ligand selected from the group consisting of alkylalcohols, arylalcohols, arylalkyl alcohols, alkylamines, arylamines, arylalkyl amines, alkylthiols, arylthiols, arylalkyl thiols and, in the case of $MBH_{4-n-a}(R^*)_n(R')_a$ and $MBH_{2-b}(R^{**}) (R')_b$, cyanide;

R" is a bidentate achiral ligand selected from the group consisting of alkyldiols, aryldiols, arylalkyl diols, alkyldiamines, aryldiamines, arylalkyl diamines, alkyldithiols, arylthiols, arylalkyl thiols, mercaptoalcohols, mercaptoamines, and aminoalcohols;

n is 1–3;
a is 0–2; and
b is 0–1, with the proviso that n+a≦3, and with the further proviso that when R** is S-BINOL, M is not Li+.

These complexes are generally obtained by admixing 1 equivalent of $MBH_4$, $MBH_3(CN)$ or $MAlH_4$ with R*, R or R*; optionally with 1–2 equivalents of an achiral ligand (R'); or optionally 1 equivalent of R". The chiral boron or aluminum hydride complexes of the present invention can be obtained from 1 equivalent of $MBH_4$ or $MAlH_4$ and 1 to 3 equivalents of a monodentate chiral ligand (R*) or a mixture of different R*s, 1 equivalent of monodentate chiral ligand (R*) and 1 equivalent of bidentate achiral ligand (R"), 1 eq. of a bidentate chiral ligand (R) or 1 eq. of a tridentate chiral ligand (R*). The chiral boron hydride complexes of the present invention can also be obtained from 1 equivalent of $MBH_3(CN)$ and 2 equivalents of R* or 1 equivalent of R**. By "monodentate," "bidentate," and "tridentate" is meant a ligand having 1, 2 or 3 active hydrogen moieties, respectively.

It will be understood that when the chiral hydride complexes are obtained from $MBH_4$ or $MAlH_4$, 1 equivalent of $MBH_4$ or $MAlH_4$ can be admixed in the presence of an organic solvent with 1–3 equivalents of R* and optionally with 1–2 equivalents of R', such that the total equivalents of R* and R' relative to $MAlH_4$ or $MBH_4$ does not exceed three; with 1 equivalent of R* and 1 equivalent of R"; with 1 equivalent of R, and optionally with 1 equivalent of R'; or with 1 equivalent of R*.

When the chiral hydride complexes are obtained from $MBH_3(CN)$, 1 equivalent of $MBH_3(CN)$ can be admixed in the presence of an organic solvent with 1–2 equivalents of R* and optionally with 1 equivalent of R', such that the total equivalents of R* and R' does not exceed 2; or with 1 equivalent of R**.

The chiral hydride complexes can also comprise a chiral or an achiral solid phase support, as discussed below. Such a chiral or achiral solid phase support is admixed with a metal hydride selected from the group consisting of $MBH_4$, $MBH_3(CN)$ and $MAlH_4$, in the presence of an organic solvent. Where the solid phase support is achiral, the solid phase support is admixed with a metal hydride selected from the group consisting of $MBH_4$, $MBH_3(CN)$ and $MAlH_4$, in the presence of a chiral ligand (R* or R**) and an organic solvent. It is to be understood that the solid phase support can have a plurality of moieties capable of forming a stable complex with $MBH_4$, $MBH_3(CN)$ or $MAlH_4$, such as hydroxyl, amino or sulfide groups. Accordingly, 1 equivalent of $MBH_4$, $MBH_3(CN)$ or $MAlH_4$ can react with up to about 1 equivalent, preferably from about 0.01 to about 0.5 equivalents, and most preferably from about 0.05 to about 0.3 equivalents of solid phase support.

$MBH_4$ and $MAlH_4$ can be obtained commercially; e.g., $NaBH_4$, $Na(CN)BH_3$, $LiBH_4$, $KBH_4$ and $LiAlH_4$ are available from Aldrich Chemical Co., Milwaukee, Wisc., and $NaAlH_4$ is available from Albemarle Corporation, Baton Rouge, La. Alternatively, $MBH_4$ and $MAlH_4$ can be prepared by synthetic methods known to those skilled in the art.

The invention also encompasses chiral boron or aluminum hydride complexes having oligomeric structures. The skilled artisan will recognize that such complexes may exist in oligomeric form.

Useful monodentate, bidentate, and tridentate chiral ligands are those that are derived from optionally protected carbohydrates, amino acids, amino alcohols, alkaloids, chiral aromatic or alkyl alcohols, chiral aromatic or alkyl amines, chiral diamines, chiral diols, chiral biaryl alcohols, chiral biaryl amines, D- or L-tartaric acid or combinations thereof, and are capable of forming chiral hydride complexes with $MBH_4$, $MBH_3(CN)$ or $MAlH_4$ such that the resulting chiral hydride complex is capable of enantioselectively reducing a carbonyl group or a carbonyl equivalent of a chemical entity. By "protected" is meant that the carbohydrates, amino acids, amino alcohols, alkaloids, chiral aromatic or alkyl alcohols, chiral aromatic or alkyl amines, chiral diamines, chiral diols, chiral biaryl alcohols, chiral biaryl amines, D- or L-tartaric acid or combinations thereof, comprise protecting groups including, but not limited to, ketals, trimethylsilyl ethers, tetrahydropyranyl ethers, triphenylmethyl ethers, benzyl ethers, etc. Examples of such protecting groups, as well as methods for their use and removal, are found in T. W. Greene, *Protective Groups in Organic Synthesis*, John Wiley & Sons, New York, 1981. Such chiral ligands have one or more chiral centers and are optically active. The chiral ligands have 1–3 active hydrogen atoms per ligand that can react with one or more hydride groups of $MBH_4$, $MBH_3(CN)$ or $MAlH_4$, so as to form a sodium, lithium or potassium boron or aluminum hydride:chiral ligand complex, with the release of $H_2$.

Useful chiral ligands include naturally occurring carbohydrates, amino acids, amino alcohols, alkaloids, chiral aromatic or alkyl alcohols, chiral aromatic or alkyl amines, chiral diamines, chiral diols, chiral biaryl alcohols, chiral biaryl amines, D- or L-tartaric acid or combinations thereof; or synthetic analogs obtained using organic synthesis methods which are known to those skilled in the art.

Preferable chiral ligands include 1,2:5,6-Di-O-isopropylidene-D-mannitol ("DIPM"); 3,5:4,6-Di-O-ethylidene-D-glucitol ("DES"); S-BINOL; (S)-1-tert-Butylamino-2,3-propanediol ("(S)-PROP"); 1,2:5,6-Di-O-cyclohexylidene-α-D-glucofuranose ("DCG"); 3-O-Benzyl-1,2:5,6-di-O-cyclohexylidene-α-D-glucofuranose ("BDCG"); 3-O-Benzyl-1,2-O-cyclohexylidene-α-D-glucofuranose ("BCG"); 2-O-Benzyl-3,5:4,6-diethylidene-D-glucidol ("BDG"); 1,3:4,6-Di-O-benzyliden-D-mannitol ("DBM"); (S,S)-1,3-Bis-(1-phenylethylamino)-2-propanol ("(S,S)-BPAP"); 1-Anilino-3,5:4,6-di-O-ethylidene-D-glucitol ("Ligand 5b"); (S)-N-isobutyl-α-phenylethylamine ("(S)-IBPA"); (R)-N-isobutyl-α-phenylethylamine ("(R)-IBPA"); (S,S)-N,N-Bis(methylbenzyl)ethylenediamine ("(S,S)-BMBE"); 1,2-O-isopropylidene-α-D-xylofuranose ("IXF"); (R)-1-tert-Butylamino-2,3-propanediol ("BAP"); 1,2-O-Cyclohexylidene-α-D-xylofuranose ("CXF"); (S)-Phenylalaninol ("(S)-PA"); (S)-N,N-(Dimethyl)phenylalaninol ("(S)-DMPA"); (3S,4S)-1-Benzyl-3,4-dihydroxypyrrolidine ("BDHP"); 1-O-Triphenylmethyl-3,5:4,6-di-O-ethylidene-D-glucitol ("TDG"); 1,3:4,6-Di-O-(ρ-anisylidene)-D-mannitol ("DAM"); 1,3:4,6-Di-O-(ρ-toluylidene)-D-mannitol ("DTM1"); 2,3-O-Cyclohexylidene-1,1,4,4-tetraphenyl-L-threitol ("CYTOL"); Di-O-cyclohexylidene-D-allofuranose ("DCAF"); Di-O-isopropylidene-D-allofuranose ("DIPAF"); 2,3:4,6-Di-O-isopropylidene-L-sorbofuranose ("DIPS"); (+)-trans-α,α'-(2,2-Dimethyl-1,3-dioxolane-4,5-diyl)bis(diphenylmethanol) ("(+)-DDM"); (−)-trans-α,α'-(2,2-Dimethyl-1,3-dioxolane-4,5-diyl)bis(diphenylmethanol) ("(−)-DDM"); (−)-8-methoxy-trans-p-menth-3-ol ("MTM"); 1,2:3,5-Di-O-benzylidene-D-glucofuranose ("DBGLU"); L-(−)-2,4:3,5-Di-O-methylidene-D-xylitol ("L-DMX"); D-(+)-2,4:3,5-Di-O-methylidene-D-xylitol ("D-DMX"); (S)-(−)-α,α-diphenyl-(1,2,3,4-tetrahydroisoquinolin-3-yl)-methanol ("DTM2"); (1R,2S)-(−)-ephedrine ("Eph"); 1,6-anhydro-β-D-glucose ("AG"); (S)-α-phenethylamine ("(S)-PEA); (S)-(−)-α, α-diphenyl-2-pyrrolidinemethanol ("DPP"); (1S,2S,3R,5R)-(+)-pinanediol ("(+)-PDOL"); (S)-2-(anilinomethyl)pyrrolidine ("AMP"); and (4R,5R)-2,2-dimethyl-α,α,α',α'-tetra-(2-naphthyl)-dioxolane-4,5-dimethanol ("β-DND"). The abbreviations of these ligands will be used to facilitate reading of this specification.

Especially preferred are those R chiral ligands having a $C_2$ axis of symmetry. By "$C_2$ axis of symmetry" is meant a molecule having a $C_2$ axis as the sole element of symmetry, and therefore not possessing reflection symmetry (no sigma plane). The R chiral ligands can also be described as "axially disymmetric."

Where the chiral boron or aluminum complexes of the present invention comprise R* but not R or R*, such complexes can comprise a mixture of up to three different R* ligands, as long as there is at least one hydride per equivalent of chiral complex available for imparting enantioselectivity to carbonyl group and carbonyl equivalent-containing substrates; or can comprise one R* ligand and one R" ligand. Where the chiral boron or aluminum complexes of the present invention comprise R**, such complexes can additionally comprise R*, as long as there is at least one hydride per equivalent of chiral complex available for imparting enantioselectivity to carbonyl group and carbonyl equivalent-containing substrates.

In addition to comprising 1–3 chiral ligands, the chiral hydride complexes of the present invention can optionally further comprise 1–2 achiral ligand(s) (R'), selected from the group consisting of alkylalcohols, arylalcohols, arylalkyl alcohols, alkylamines, arylamines, arylalkyl amines, alkylthiols, arylthiols, arylalkyl thiols and, in the case of chiral borohydride complexes, cyanide. The R' achiral ligands have 1 active hydrogen atom per ligand and can react with one or more hydride groups of $MBH_4$ or $MAlH_4$, preferably with one or more hydride groups of a sodium, lithium or potassium boron or aluminum hydride:chiral ligand complex, so as to form a sodium, lithium or potassium boron or aluminum hydride:chiral ligand:achiral ligand complex with the release of $H_2$. It is important that if the present chiral hydride complexes comprise R', there must be at least one hydride per equivalent of chiral complex available for imparting enantioselectivity to carbonyl group and carbonyl equivalent-containing substrates. In other words, if the present chiral hydride complexes comprise R', the total equivalents of R* or R**, and R', relative to $MBH_4$ or $MAlH_4$, cannot exceed three. In addition, if the present chiral hydride complexes comprise R', the total equivalents of R* and R', relative to $MBH_3(CN)$, cannot exceed two.

Furthermore, the chiral hydride complexes of the present invention can comprise 1 bidentate achiral ligand R", selected from the group consisting of alkyldiols, aryldiols, arylalkyl diols, alkyldiamines, aryldiamines, arylalkyl diamines, alkyldithiols, arylthiols, arylalkyl thiols, mercaptoalcohols, mercaptoamines, and aminoalcohols selected from the group consist. Because R" comprises two active hydrogen moieties, it is preferable that when R" is used as an achiral ligand, it is used in conjunction with R*.

The R' and R" achiral ligands can be used to optimize the yield of the product of reduction of the carbonyl group- or carbonyl equivalent-bearing chemical entity with the chiral hydride complexes of the present invention, or to optimize the enantiomeric excess of a desired enantiomeric product.

Alkylalcohol, alkylamine and alkylthiol ligands useful as R' include $C_1$–$C_{18}$, preferably $C_1$–$C_{10}$ and most preferably $C_1$–$C_6$ alkylalcohols, alkylamines and alkylthiols. Preferable alkylalcohols include methanol, ethanol, 2-methoxyethanol, n-propanol, iso-propanol, n-butanol, iso-butanol, sec-butanol, tert-butanol 1-methylcyclobutanol and the like. Preferable alkylamines include methylamine, ethylamine, dimethylamine, diethylamine, diisopropylamine dicyclohexylamine and the like. Preferable alkylthiols include methanethiol, ethanethiol, propanethiol, butanethiol and the like.

Arylalcohols, arylamines and arylthiols useful as R' include phenyl- and naphthylalcohols, -amines and -thiols optionally substituted with one or more $C_1$–$C_6$ alkyl or alkoxy groups. Preferable arylalcohols include phenol, o-tert-butylphenol, p-tert-butylphenol, 1-naphthol and 2-naphthol. Preferable arylamines include aniline, p-methoxyaniline, diphenylamine and the like. Preferable arylthiols include thiophenol, o-methoxythiophenol, p-methoxythiophenol and the like.

Arylalkyl alcohols, arylalkyl amines and arylalkyl thiols useful as R' include phenyl- and naphthyl-substituted alkanols, including benzylalcohol, alkylamines including benzylamine, alkylthiols including benzylthiol.

Alkyldiol, alkyldiamine and alkyldithiol ligands useful as R" include $C_1$–$C_{18}$, preferably $C_1$–$C_{10}$ and most preferably $C_1$–$C_6$ alkyldiols, alkyldiamines and alkyldithiols. Preferable alkyldiols include ethylene glycol, propylene glycol, 1,4-butanediol, 1,5-pentanediol, 1,6-hexanediol and the like. Preferable alkyldiamines include ethylene diamine, 1,3-propanediamine, 1,4-butanediamine and the like. Preferable alkyldithiols include ethanedithiol, 1,3-propanedithiol, 1,4-butanedithiol, 2,3-butanedithiol and the like.

Aryldiols, aryldiamines and aryldithiols useful as R" include phenyl- and naphthyldiols, -diamines and -dithiols optionally substituted with one or more $C_1$–$C_6$ alkyl or alkoxy groups. Preferable aryldiols include catechol, resorcinol, 3-methoxycatechol, 5-methoxyresorcinol, and the like. Preferable aryldiamines include 1,2-phenylenediamine, 1,3-phenylenediamine, 4-methoxy-1,2-phenylenediamine, and the like. Preferable aryldithiols include 1,2-benzenedithiol, 1,3-benzenedithiol, and the like.

Arylalkyl diols, arylalkyl diamines and arylalkyl dithiols useful as R" include phenyl- and naphthyl-substituted diols, including 2-hydroxybenzyl alcohol and 3-hydroxylbenzyl alcohol; aralkyl diamines including 2-aminobenzylamine; and aralkyl dithiols including 2-thiobenzyl mercaptan.

Useful R" ligands also comprise mercaptoalcohols, such as mercaptoethanol, 3-mercaptobutanol and the like; mercaptoamines, such as 2-aminoethanethiol and the like; and aminoalcohols, such as aminoethanol, 3-aminobutanol, and the like.

The present chiral boron or aluminum hydride complexes are synthesized such that the $MBH_4$, $MBH_3(CN)$ or $MAlH_4$; chiral ligand (R*, R or R*) and optionally the achiral ligands (R' or R") are admixed in the presence of an organic solvent lacking active hydrogens or other groups capable of reacting with hydride groups. Suitable organic solvents include, but are not limited to alkyl hydrocarbons, such as pentane, hexane and heptane; cyclic or acylic ethers, such as THF and diethyl ether; optionally substituted aromatics, such as benzene, toluene, xylene and chlorobenzene; polyethers such as diglyme and triglyme; other solvents that are inert to hydride reducing agents; and mixtures thereof. Preferably, the organic solvent is THF, diglyme or mixtures thereof. The solution of the organic solvent and the chiral hydride complex thus obtained can be used directly as a composition for enantioselectively reducing a chemical entity having a carbonyl group or a carbonyl equivalent, or can be concentrated, optionally in vacuo, to afford a chiral hydride complex free from solvent. In the latter case, the chiral hydride complex can be stored, preferably under an inert atmosphere, for future use.

In one embodiment of the invention, the chiral hydride complexes are prepared by admixing in the presence of organic solvent 1 equivalent of $MBH_4$ or $MAlH_4$ with 3 equivalents of R*.

In another embodiment of the invention, the chiral hydride complexes are prepared by admixing in the presence of organic solvent 1 equivalent of $MBH_4$ or $MAlH_4$ with 2 equivalents of R*; and 1 equivalent of R'.

In another embodiment of the invention, the chiral hydride complexes are prepared by admixing in the presence of organic solvent 1 equivalent of $MBH_4$ or $MAlH_4$ with 1 equivalent of R*; and 2 equivalents of R'.

In another embodiment of the invention, the chiral hydride complexes are prepared by admixing in the presence of organic solvent 1 equivalent of $MBH_4$ or $MAlH_4$ with 1 equivalent of R*; and 1 equivalent of R".

In another embodiment of the invention, the chiral hydride complexes are prepared by admixing in the presence of organic solvent 1 equivalent of $MBH_4$ or $MAlH_4$ with 1 equivalent of R**; and 1 equivalent of R'.

In another embodiment of the invention, the chiral hydride complexes are prepared by admixing in the presence of organic solvent 1 equivalent of $MBH_4$ or $MAlH_4$ with 1 equivalent of R***.

In another embodiment of the invention, the chiral hydride complexes are prepared by admixing in the presence of organic solvent 1 equivalent of $MBH_4$ or $MAlH_4$ with 2 equivalents of R*.

In another embodiment of the invention, the chiral hydride complexes are prepared by admixing in the presence of organic solvent 1 equivalent of $MBH_4$ or $MAlH_4$ with 1 equivalent of R**.

In another embodiment of the invention, the chiral hydride complexes are prepared by admixing in the presence of organic solvent 1 equivalent of $MBH_4$ or $MAlH_4$ with 1 equivalent of R*.

In a further embodiment of the invention, the chiral hydride complexes are prepared by admixing in the presence of organic solvent 1 equivalent of $MBH_3(CN)$ with 1 equivalent of R*.

In a further embodiment of the invention, the chiral hydride complexes are prepared by admixing in the presence of organic solvent 1 equivalent of $MBH_3(CN)$ with 1 equivalent of R* and 1 equivalent of R'.

In a further embodiment of the invention, the chiral hydride complexes are prepared by admixing in the presence of organic solvent 1 equivalent of $MBH_3(CN)$ with 2 equivalents of R*.

In a further embodiment of the invention, the chiral hydride complexes are prepared by admixing in the presence of organic solvent 1 equivalent of $MBH_3(CN)$ with 1 equivalent of R**.

The chiral hydride complexes can be prepared by adding the $MBH_4$ or $MAlH_4$, preferably as a solution in organic solvent, to the chiral ligand(s), preferably as a solution in organic solvent, or to a mixture of chiral and achiral ligands, preferably as a solution in organic solvent. Alternatively, the chiral ligand(s), preferably as a solution in organic solvent, can be added to the $MBH_4$ or $MAlH_4$, preferably as a solution in organic solvent, optionally followed by addition of an achiral ligand, preferably as a solution in organic solvent. Preferably, an organic solution of the chiral ligand(s) is added to an organic solution of $MBH_4$ or $MAlH_4$, optionally followed by the addition of an organic solution of an achiral ligand (R' or R"). Most preferably, the organic solvent is THF, diglyme or mixtures thereof. Because the chiral boron or aluminum hydride complexes of the present invention are moisture sensitive, the chiral hydride complexes are preferably prepared under an inert atmosphere such as nitrogen or argon.

When cyanide is used as an achiral ligand in the case of the present chiral borohydride complexes, $MBH_3(CN)$ can be prepared from the reaction of $BH_3$ with MCN, or preferably, $MBH_3(CN)$ is obtained commercially (e.g., in the case of $NaBH_3(CN)$, Aldrich Chemical Co., Milwaukee, Wis.). In this case, an organic solution of $MBH_3(CN)$ can be added to an organic solution of chiral ligand(s), or vice versa.

The admixture of the $MBH_4$, $MBH_3(CN)$ or $MAlH_4$; the chiral ligand(s); and optionally the achiral ligand can occur from about $-78°$ C. to reflux temperatures, preferably from about $-78°$ C. to about $40°$ C. and most preferably from about $-78°$ C. to about room temperature. The reaction mixture comprising the organic solution of the $MBH_4$, $MBH_3(CN)$ or $MAlH_4$; the chiral ligand(s); and optionally achiral ligands R' or R", can stir for 1 min. to 10 days, preferably from 2 min. to 7 days and most preferably from 5 min. to 3 days. Those skilled in the art will recognize that enantioselectivity tends to increase at lower temperatures.

COMPOSITIONS COMPRISING CHIRAL HYDRIDE COMPLEXES

The present invention provides compositions useful for enantioselectively reducing a chemical entity having a carbonyl group or a carbonyl equivalent. Such compositions comprise 1 equivalent of sodium cation ($Na^+$), lithium cation ($Li^+$) or potassium cation ($K^+$); 1 equivalent of boron cation ($B^{3+}$) or aluminum cation ($Al^{3+}$); 1–3 equivalents of hydride; 1–3 equivalents of a monodentate ligand (R*), 1 equivalent of a bidentate ligand (R) or tridentate ligand (R*); optionally 1–2 equivalents of a monodentate achiral ligand (R') or 1 equivalent of a bidentate achiral ligand (R"), wherein R*, R, R* and R' are defined above; and preferably an inert organic solvent. It is to be understood that the compositions that comprise 1 equivalent of R* can comprise 1–2 equivalents of R', or 1 equivalent of R". The compositions that comprise R** can comprise 1 equivalent of R'.

In one embodiment of the invention, the chiral hydride complexes comprise 1 equivalent of sodium cation ($Na^+$), lithium cation ($Li^+$) or potassium cation ($K^+$); 1 equivalent of boron cation ($B^{3+}$) or aluminum cation ($Al^{3+}$); 1 equivalent of hydride; and 3 equivalents of R*.

In another embodiment of the invention, the chiral hydride complexes comprise 1 equivalent of sodium cation ($Na^+$), lithium cation ($Li^+$) or potassium cation ($K^+$); 1 equivalent of boron cation ($B^{3+}$) or aluminum cation ($Al^{3+}$); 1 equivalent of hydride; 2 equivalents of R*; and 1 equivalent of R'.

In another embodiment of the invention, the chiral hydride complexes comprise 1 equivalent of sodium cation ($Na^+$), lithium cation ($Li^+$) or potassium cation ($K^+$); 1 equivalent of boron cation ($B^{3+}$) or aluminum cation ($Al^{3+}$); 1 equivalent of hydride; 1 equivalent of R*; and 2 equivalents of R'.

In another embodiment of the invention, the chiral hydride complexes comprise 1 equivalent of sodium cation ($Na^+$), lithium cation ($Li^+$) or potassium cation ($K^+$); 1 equivalent of boron cation ($B^{3+}$) or aluminum cation ($Al^{3+}$); 1 equivalent of hydride; 1 equivalent of R*; and 1 equivalent of R".

In another embodiment of the invention, the chiral hydride complexes comprise 1 equivalent of sodium cation ($Na^+$), lithium cation ($Li^+$) or potassium cation ($K^+$); 1 equivalent of boron cation ($B^{3+}$) or aluminum cation ($Al^{3+}$); 1 equivalent of hydride; 1 equivalent of R**; and 1 equivalent of R'.

In another embodiment of the invention, the chiral hydride complexes comprise 1 equivalent of sodium cation ($Na^+$), lithium cation ($Li^+$) or potassium cation ($K^+$); 1 equivalent of boron cation ($B^{3+}$) or aluminum cation ($Al^{3+}$); 1 equivalent of hydride; and 1 equivalent of R***.

In another embodiment of the invention, the chiral hydride complexes comprise 1 equivalent of sodium cation ($Na^+$), lithium cation ($Li^+$) or potassium cation ($K^+$); 1 equivalent of boron cation ($B^{3+}$) or aluminum cation ($Al^{3+}$); 2 equivalents of hydride; and 2 equivalents of R*.

In another embodiment of the invention, the chiral hydride complexes comprise 1 equivalent of sodium cation ($Na^+$), lithium cation ($Li^+$) or potassium cation ($K^+$); 1 equivalent of boron cation ($B^{3+}$) or aluminum cation ($Al^{3+}$); 2 equivalents of hydride; and 1 equivalent of R**.

In another embodiment of the invention, the chiral hydride complexes comprise 1 equivalent of sodium cation ($Na^+$), lithium cation ($Li^+$) or potassium cation ($K^+$); 1 equivalent of boron cation ($B^{3+}$) or aluminum cation ($Al^{3+}$); 3 equivalents of hydride; and 1 equivalent of R*.

The present invention also encompasses compositions which comprise $Na^+$, $Li^+$ or $K^+$; $B^{3+}$ or $Al^{3+}$; hydride; R*, R or R*; and optionally R' in stoichiometries outside of the ranges described above. Such compositions comprise chiral hydride complexes having oligomeric structure.

The present compositions useful for enantiomerically reducing a chemical entity having a carbonyl group or carbonyl equivalent are obtained by the methods described above.

By "inert organic solvent" is meant that the organic solvent lacks active hydrogens or other groups capable of reacting with the hydride species. Suitable organic solvents include, but are not limited to alkyl hydrocarbons, such as pentane, hexane and heptane; cyclic or acylic ethers, such as THF and diethyl ether; optionally substituted aromatics, such as benzene, toluene, xylene and chlorobenzene; polyethers such as diglyme and triglyme; other solvents that are inert to hydride reducing agents; and mixtures thereof. Preferably, the organic solvent is THF, diglyme or mixtures thereof.

The present compositions encompass those which lack organic solvent. After admixing in the presence of organic solvent the $MBH_4$, $MBH_3(CN)$ or $MAlH_4$; chiral ligand(s); and optionally the achiral ligand, the compositions can be concentrated, preferably in vacuo, so as to obtain a solid, solvent-free chiral hydride complex. Such solvent-free chiral hydride complexes are preferably stored under an inert atmosphere, e.g., nitrogen or argon, in a dark, air tight vessel. When stored in this manner, the solvent-free chiral hydride complexes should be stable at room temperature for several months, and at low (<0° C.) temperatures for several years.

The chiral boron or aluminum hydride complex compositions of the present invention optionally comprise other agents useful for imparting and/or fine-tuning enantioselectivity to carbonyl group and carbonyl equivalent-containing substrates. Such agents include chiral alkoxide bases; trialkylamines, such as triethylamine; and Lewis acids such as aluminum chloride, titanium tetrachloride, boron trifluoride and the like, and can be added to the present compositions at any stage of the synthesis of the present chiral hydride complexes.

The present compositions are useful for enantioselectively reducing a chemical entity having a carbonyl group or a carbonyl equivalent. By "enantioselectively reducing" is meant delivering an equivalent of hydride from a present chiral boron or aluminum hydride complex preferentially to one face of a prochiral chemical entity, so as to obtain an enantiomeric excess of a particular reduction product thereof, or in the case where the prochiral chemical entity contains at least one chiral center, a diastereomeric excess of a particular reaction product thereof. By "carbonyl equivalent" is meant an organic moiety derived from a carbonyl group and capable of undergoing asymmetric reduction to yield an asymmetric reduction product. Such carbonyl equivalents include ketones, thioketones, imines (Schiff bases), unsymmetrical diaryl or dialkyloximes, unsymmetrical diaryl or dialkyloxime ethers, epoxides, thioepoxides, enamines, and the like. Such carbonyl equivalents are available commercially from, for example, Aldrich Chemical Co., Milwaukee, Wis., or obtainable from conventional organic synthesis via means known to those skilled in the art.

In addition, the present compositions are useful for reducing a carbon-carbon double bond of an $\alpha,\beta$-unsaturated carbonyl, or $\alpha,\beta$-unsaturated carbonyl equivalent system, via 1,4-addition of hydride to the $\beta$-carbon atom the $\alpha,\beta$-unsaturated carbonyl or $\alpha,\beta$-unsaturated carbonyl equivalent system. Such reductions are advantageously conducted at temperatures ranging from about −78° C. to room temperature, preferably from about −78° C. to about 0° C., and in inert organic solvents described above.

SOLID PHASE CHIRAL HYDRIDE COMPLEXES

The chiral hydride complexes of the present invention can comprise a solid phase support, allowing the chiral hydride complexes to be more easily synthesized, weighed and transferred, and recovered from a reaction mixture. Such solid phase supports can be chiral or achiral. Suitable chiral solid phase supports include, but are not limited to, optionally protected chiral polysaccharides, such as $\alpha$-, $\beta$- or $\gamma$-cyclodextrin or chitosan, which have pendant moieties that are capable of forming a stable complex with $MBH_4$, $MBH_3(CN)$ and $MAlH_4$. Preferably, the solid phase support is a chiral polysaccharide. As used in this context, "protected" means that at least one, but less than all, of the polysaccharide hydroxyl groups is protected with a protecting group, such as one found in T. W. Greene, *Protective Groups in Organic Synthesis,* John Wiley & Sons, New York, 1981.

Suitable achiral solid phase supports include, but are not limited to, polyacrylic acid, polystyrene, polyvinyl alcohol, poly(dimethylacrylamide)-grafted styrene co-divinylbenzene, polyamide resin, polystyrene grafted with polyethylene glycol, polydimethylacrylamide resin, and polyacrylamide.

Where the solid phase support is chiral, the solid phase support is admixed in the presence of an organic solvent with $MBH_4$, $MBH_3(CN)$ or $MAlH_4$, optionally in the presence of an achiral ligand, according to the methods described above, to provide a chiral hydride complex comprising a solid phase support. Where the chiral solid phase support comprises a plurality of moieties capable of forming a stable complex with $MBH_4$, $MBH_3(CN)$ or $MAlH_4$, e.g., hydroxyl, amino or sulfide groups, some of these moieties can be optionally protected with one or more protecting group prior to reaction with $MBH_4$, $MBH_3(CN)$ or $MAlH_4$. In this regard, the use of one or more protecting group will prevent all of the hydrides of $MBH_4$, $MBH_3(CN)$ and $MAlH_4$ from reacting with the moieties and ensure that the resulting chiral hydride complex has at least one hydride available for reaction with a carbonyl group or carbonyl-equivalent containing substrate. Following reaction with $MBH_4$, $MBH_3(CN)$ or $MAlH_4$, a protecting-group bearing solid phase support can optionally be deprotected. Suitable protecting groups and methods for use and deprotection can be found in T. W. Greene, *Protective Groups in Organic Synthesis,* John Wiley & Sons, New York, 1981.

Where the solid phase support is achiral, the achiral solid phase support can be covalently bonded to a chiral ligand (R*, R or R*), or to an achiral ligand (R' or R") used in conjunction with R* or R**, prior to reaction with $MBH_4$, $MBH_3(CN)$ or $MAlH_4$ via the above-described methods. In this case, the chiral or achiral ligand bears a reactive group, such as a carboxyl (or its equivalent) or an epoxy group, capable of forming a covalent bond with a reactive moiety, e.g., a hydroxyl, amino or sulfide group, on an achiral solid phase support. Such a covalent bond is formed by admixing the reactive group-bearing chiral or achiral ligand with the solid phase support in the presence of a suitable reaction solvent, such as an alkyl hydrocarbon, e.q., pentane, hexane or heptane; a cyclic or acylic ether, e.q., THF or diethyl ether; an optionally substituted aromatic, e.g., benzene, toluene, xylene or chlorobenzene; a polyether e.g., diglyme or triglyme; any other solvent that is inert to hydride reducing agents; and mixtures thereof, optionally with heating. Preferably, the reactive moiety of the achiral solid phase support is an amino or hydroxyl group, and the reactive group of the chiral or achiral ligand is a carboxyl group.

Alternatively, the achiral solid phase support can serve as an achiral ligand that reacts with $MBH_4$, $MBH_3(CN)$ or $MAlH_4$, preferably in the presence of a monodentate or bidentate chiral ligand (R* or R**) and an organic solvent, to form a chiral hydride complex.

METHODS FOR USING THE CHIRAL HYDRIDE COMPLEXES

The present chiral boron or aluminum hydride complexes, or compositions comprising the chiral hydride complexes, are useful for obtaining an enantiomeric excess of a reduction product. It will be understood that the reduction product of a chiral hydride complex and a carbonyl group will be an alcohol. Where the carbonyl equivalent is a thioketone, the reduction product will be mercaptan. Where the carbonyl equivalent is an imine, the reduction product will be an amine. Where the carbonyl equivalent is an oxime or an oxime ether, the reduction product will be a species having an —NH—O— group. Where the carbonyl equivalent is an epoxide, the reduction product will be an alcohol. Where the carbonyl equivalent is a thioepoxide, the reduction product will be a mercaptan. Where the carbonyl equivalent is an enamine, the reduction product will be an amine.

Reduction of the carbonyl group or carbonyl equivalent is achieved by admixing the desired chiral hydride complex or composition comprising the chiral hydride complex with the substrate to be reduced. By "substrate to be reduced" is meant a chemical entity having a carbonyl group or carbonyl equivalent. Such admixture can be accomplished by adding the chiral hydride complex, preferably as a composition comprising the chiral hydride complex and organic solvent, to a substrate to be reduced, preferably as a solution in organic solvent. Alternatively, the substrate to be reduced, preferably as a solution in organic solvent, can be added to the chiral hydride complex, preferably as a composition comprising the chiral hydride complex and organic solvent. Preferably, an organic solution of the substrate to be reduced is added dropwise to a composition comprising the chiral hydride complex and organic solution. Most preferably, the reduction is achieved by freshly preparing a composition comprising the chiral hydride complex and organic solvent, via methods described above, and thereafter adding to the complex an organic solution of the substrate to be reduced, such that the synthesis of the chiral hydride complex and reduction of the desired substrate are achieved in a one-pot method.

Organic solvents useful for reduction using the present chiral hydride complexes are those that are unreactive to hydride and include, but are not limited to alkyl hydrocarbons, such as pentane, hexane and heptane; cyclic or acylic ethers, such as THF and diethyl ether; optionally substituted aromatics, such as benzene, toluene, xylene and chlorobenzene; polyethers such as diglyme and triglyme; and mixtures thereof.

Reduction of the desired substrate with the present chiral hydride complexes can occur at a temperature from −78° C. to the reflux temperature of the solvent used in the reaction mixture, preferably from −70° C. to room temperature. Reaction times may vary from several minutes to up to 7 days, depending upon the reaction temperature and nature of chiral hydride complex and substrate.

The ratio of chiral hydride complex to substrate to be reduced can range from about 15:1 to about 1:1, preferably from about 12:1 to about 3:1. Because the chiral hydride complexes of the present invention are moisture sensitive, the reductions are preferentially conducted under an inert atmosphere such as nitrogen or argon.

Once the chiral hydride complex is admixed with the substrate to be reduced, and reacted therewith such that the substrate to be reduced is reduced by the chiral hydride complex, the reaction is quenched, typically with water, aqueous acid, aqueous ammonium chloride, aqueous tartrate solution, or the like.

In addition, the present chiral hydride complexes can be used in conjunction with other hydride reducing agents known to those skilled in the art, such that the present complexes are auxiliary reducing agents. In this instance, the present complexes are present in less than stoichiometric amounts, whereas the other hydride reducing agents are present in stoichiometric or excess quantities. In this instance, the present chiral hydride complexes are continuously regenerated via reaction with the other hydride reducing agent(s).

EXAMPLES

The following series of Examples are presented by way of illustration and not by way of limitation on the scope of the invention.

EXAMPLE: SYNTHESIS OF CHIRAL HYDRIDE COMPLEXES CHIRAL LIGANDS SYNTHESIZED

Examiple 1

1,2:5,6-Di-O-isopropylidene-D-mannitol (Ligand 2) (DIPM). Ligand 2 was prepared according to the method described in J. Am. Chem. Soc., 1945, 67, 338. 20 g of D-mannitol, 100 g of acetone and 120 g of zinc chloride were heated at 20° C. for 72 h to afford 15.6 g (54%) crude product of the above-titled compound (80% purity by $^{13}C$ NMR) and 8.5 g (29%) following recrystallization: mp.= 122–23° C.; $^{13}C$ NMR $(CDCl_3)$ δ25.17, 26.70, 66.71, 71.08, 76.10, 109.34.

Example 2

1,2:5,6-Di-O-isopropylidene-D-mannitol (Ligand 2) (DIPM). DIPM was prepared according to the method described in J. Org. Chem., 1991, 56, 4056. A mixture of 37.5 g of D-mannitol, 60 mL of 2,2-dimethoxypropane and 37 mg of $SnCl_2$ were heated at reflux in glyme (74° C.) until a clear solution was obtained (approximately 1 h), and then for an additional 30 min, to provide 42 g (39%) of the above-titled compound: mp.=122–23° C.; $^{13}C$ NMR $(CDCl_3)$ δ25.17, 26.70, 66.71, 71.08, 76.10, 109.34.

Example 3

3,5:4,6-Di-O-ethylidene-D-glucitol (Ligand 5a) (DES). A mixture of D-glucitol and excess paraacetaldehyde were stirred in the presence of concentrated HCl at 20° C. for 10 h to provide 1,2:3,5:4,6-tri-O-ethylidene, which was deprotected at the 1,2-hydroxyl groups using acetic acid at 23° C. to afford 37% of the title compound as a white solid: mp.=210–12° C. (from ethanol); $[\alpha_D^{20}]$ +13.5 (c 4.1; $H_2O$); $^1H$ NMR $(CD_3OH)$ δ3.67 and 3.53 (m, H-1), 3.78 (d, H-2), 3.57 (d, H-3), 3.79 (t, H-4), 3.52 (q, H-5), 3.87–3.96 (m, H-6), 4.75 (q, H-7 and H-9), 1.28 and 1.26 $(CH_3)$; $^{13}C$ NMR $(CD_3OH)$ δ64.0 (C-1), 69.8 (C-2), 78.8 (C-3), 69.3 (C-4), 71.6 (C-5), 70.6 (C-6), 99.78 and 99.94 (C-7 and C-9), 20.99 and 20.92 (C-8 and C-10).

Example 4

Diisopropyl (R,R)-tartrate. Diisopropyl (R,R)-tartrate was prepared according to the procedure described in J. Am.

Chem. Soc., 1981, 6237. 400 g of (R,R)-tartaric acid, 400 mL of isopropanol and 5 g of p-TsOH were heated in refluxing benzene to afford, following distillation, 201 g (55%) of the above-titled compound: bp.=103–105° C. (2 torr) (lit. 152° C. (12 torr)).

Example 5

N,N,N',N'-Tetramethyl-(R,R)-tartaramide. N,N,N',N'-Tetramethyl-(R,R)-tartaramide was obtained according to the procedure described in Org. Syn. 61, 24. A mixture of 23.4 g of the product of Example 4 and 13.5 g of dimethylamine was stirred in methanol at 25° C. for 24 h to afford 18.2 g (90%) of the above-titled compound following crystallization from EtOH: mp.=186° C. (lit. 185–88° C.).

Example 6

R,R-(+)-2,3-Dimethoxy-N,N,N',N'-tetramethylsuccinamide. R,R-(+)-2,3-Dimethoxy-N,N,N',N'-tetramethylsuccinamide was obtained according to the procedure described in Org. Syn. 61, 24. A mixture of 10 g of the product of Example 5 and 15.75 g of dimethylsulfate in 50% $KOH/CH_2Cl_2$ was stirred at 25° C. for 6 h to afford 7.9 g (70%) of the above-titled compound following crystallization: mp.=63–64° C.

Example 7

R,S-Binol. R,S-Binol was obtained according to the procedure described in Ber., 1926, 2160. A mixture of 60 g of β-naphthol and 132 g of $FeCl_3.6H_2O$ was heated in boiling water to afford 39 g (65%) of the above-titled compound following crystallization: mp.=219° C.

Example 8

S-Binol. S-Binol was obtained according to the method described in Chem. Lett. 1988, 1371 and in J. Org. Chem. 1988, 53, 3607. To 50 g of the product of Example 7 and 40.6 g of the product of Example 6 was added a mixture of 200 mL of benzene and 60 mL of hexane. To the resulting (S)-binol/R,R-(+)-2,3-dimethoxy-N,N,N',N'-tetramethylsuccinamide complex was added 1 eq. hydrazine to afford 33.7 g of the title compound following recrystallization.

Example 9

(S)-1-tert-Butylamino-2,3-propanediol (Ligand 3) ((S)-PROP). (S)-Glycidol was added dropwise, with stirring, to a mixture of 54.7 g of tert-butylamine and 25 mL of water, heated at reflux. The resulting mixture was heated at reflux for 12 h, and was thereafter allowed to cool to room temperature. The mixture was concentrated in vacuo and was treated with ether to effect crystallization. 28.6 g (78%) of crystalline product was thus obtained: $^1$H NMR ($CDCl_3$) δ1.0 (s, $C(CH_3)_3$), 2.4–2.6 (m), 3.3–4.2 (m); 13C NMR ($CDCl_3$) δ28.6 (3 $CH_3$), 45.2 ($CH_2NH$), 50.2 ($C(CH_3)_3$), 65.5 ($CH_2OH$), 70.6 (CHOH).

Example 10

1,2:5,6-Di-O-cyclohexylidene-α-D-glucofuranose (Ligand 12) (DCG). DCG was prepared according to the procedure described in J. Am. Chem. Soc., 1949, 71, 3072. A mixture of 90 g of α-D-glucose, 200 mL of cyclohexanone and 13 mL of sulfuric acid was allowed to stir at 20° C. for 12 h to afford 43.9 g (29%) of the above-titled compound, after two crystallizations: mp.=130.5–131.5° C. (lit. 131.1–132.4° C.).

Example 11

3-O-Benzyl-1,2:5,6-di-O-cyclohexylidene-α-D-glucofuranose (BDCG). A mixture of 40 g of DCG obtained from Example 10, 138 mL of benzyl chloride and 92.5 g of KOH was heated at 150° C. for 4 h to afford 45.5 g of the above-titled compound.

Example 12

3-O-Benzyl-1,2-O-cyclohexylidene-α-D-glucofuranose (Ligand 9b) (BCG). A mixture of 20 g of BDCG obtained from Example 11 and 75 mL of $AcOH/H_2O$ (3:1) were heated at 73° C. for 4 h to afford 8.38 g (52%) of the above-titled compound: bp.=200–205° C. (0.005 torr) (lit. 200° C. (0.005 torr)).

Example 13

2-O-Benzyl-3,5:4,6-diethylidene-D-glucidol (Ligand 5c) (BDG). 2-O-Benzyl-3,5:4,6-diethylidene-D-glucidol (BDG) was obtained according to the procedure of Izv. Akad. Nauk. SSSR, Ser. Khim. 1993 (4), 776 (Russ. Chem. Bull. 1993 (4), 744 (Engl. Trans.)). A mixture of 7 g of DES obtained from Example 3, 4.5 g of benzyl chloride and 2 g of KOH in dinethylsulfoxide was allowed to stir at 20° C. for 3 h. The reaction product was chromatographed on Aluminiumoxid 60 $\lambda_{254}$ Type E (Merck) using 5:1 $Et_2O:CHCl_3$ to afford 6 g (64.7%) of the title compound: mp.=78° C.; $[\alpha]_D^{20}$ –13.55° (c=1, in $CHCl_3$); $^1$H NMR ($CDCl_3$, 250 MHz) δ1.32 and 1.40 (d, 6H, $CH_3$), 3.60–3.89 (m, 6H, $H_{a-e}$) 4.13 (d, 2H, $CH_2Ph$), 4.49–4.58 (m, 4H, $H_{f-g}$), 7.28 (m, 5H, $C_6H_5$); $^{13}$C NMR ($CDCl_3$, 75.5 MHz) δ61.3 ($C_a$), 77.2 ($C_b$), 76.5 ($C_c$), 68.0 ($C_d$), 69.6 ($C_e$), 69.2 ($C_f$) 98.2 and 98.3 ($C_g$) and 20.5 and 20.7 ($C_h$).

Example 14

1,3:4,6-Di-O-benzyliden-D-mannitol (Ligand 7) (DBM). DBM was obtained according to the method described in J. Chem. Soc., I, 1977, 1123 or by the following procedure. A mixture of 12.5 g of D-mannitol, 12.5 g of benzaldehyde in 40 mL of dimethylformamide was treated with 5 mL of sulfuric acid added in one portion. The resulting mixture was allowed to stand at room temperature for 72 h and then poured into a mixture of 5 g of potassium carbonate, 0.5 L of ice water covered with a layer of hexane. The hexane layer containing unreacted benzaldehyde was removed and the aqueous layer was allowed to stand at 5–10° C. whereupon a white, cheese-like solid deposited thereon. The aqueous layer was filtered, and the solid air-dried and recrystallized from $CHCl_3$ to afford 13.3 g (53%) of the above-titled compound as white crystals. The resulting white crystals were washed with dry hexane (2×10 mL) and benzene (10 mL), and then dissolved in hot benzene. The benzene solution was evaporated and the resulting solid residue dried over $P_2O_5$ in an Abderhalden apparatus for 18 h at 40° C./0.3 torr to provide an analytical specimen melting at 152–53° C. (189–91° C. (MeOH)): $^1$H NMR (90 MHz, $CDCl_3$) δ3.54–3.65 (m, 2H, H-2 and H-5), 4.0 (d, 4H, H-1 and H-6), 4.22 (d, 2H, H-3 and H-4), 4.38 (br. s., 2H, OH), 5.52 (c, 2H, H-7 and H-8), 7.24–7.48 (m, Ph, Ph); $^{13}$C δ58.8 (C-3 and C-4), 70.55 (C-2, C-5), 78.1 (C-1, C-6), 100.34 (C-7, C-8), 125.49, 127.05, 127.17, 137.77 (Ph groups).

Example 15

(S,S)-1,3-Bis-(1-phenylethylamino)-2-propanol ((S,S)-BPAP). A mixture of 2.57 mL of (S)-phenethylamine and 0.39 mL of epichlorohydrin in 20 mL of methanol was allowed to reflux for 30 min. The reaction mixture was concentrated in vacuo then diluted with 5 mL of HCl-saturated isopropanol. Crystallization afforded the dihydrochloride salt (66%) of the above-titled compound. The resulting dihydrochloride salt was neutralized with NaOH and extracted into toluene to afford the above-titled compound in its free-base form: (dihydrochloride salt) decomp. point=255° C.; $[\alpha]_D^{22}$ =−36 (c=2.0, MeOH); $^1$H NMR (200 MHz, 1:1 CDCl$_3$: CCl$_4$) δ1.5 (d, 2 CH$_3$), 2.3–2.8 (m, 2 CH$_2$N,), 3.2 (br. s, 2 NH, OH), 3.7–4.0 (2 CHN+CHO), 7.1–7.6 (m, 10H, arom.); $^{13}$C NMR (200 MHz, 1:1 CDCl$_3$: CCl$_4$) δ24.20 (2 CH$_3$), 51.3, 51.75 (2 CH$_2$N), 68.55 (CHO), 126.50, 127.0, 128.45 (3 CH arom.), 144.7 (1C arom.).

Example 16

1-Chloro-3,5:4,6-di-O-ethylidene-D-glucitol. A mixture of 2.34 g of DES obtained from Example 3, 5.24 g of triphenylphosphine, 80 mL of pyridine and 15.4 g of carbon tetrachloride were heated at 55° C. for 2 h. The resulting reaction mixture was chromatographed on Aluminiumoxid 60 λ$_{254}$ Type E (Merck) using CHCl$_3$, then CHCl$_3$:CH$_3$OH (10:1—3:1, v/v) to give 0.75 g (30%) of the above-titled compound as white crystals (R$_f$=0.41): mp.=142° C. (from benzene-hexane); $^1$H NMR (90 MHz, CDCl$_3$) δ1.32 and 1.43 (d, 6H, CH$_3$), 3.50 (s, 1H, OH), 3.60–3.90 (m, H$_{a-e}$), 4.08–4.28 (m, 2H, H$_f$), 4.71–4.80 (m. 2H, H$_g$); $^{13}$C NMR (75.5 MHz, CDCl$_3$) δ47.7 (C$_a$), 67.7 (C$_b$) , 77.5 (C$_c$), 68.2 (C$_d$), 69.9 (C$_e$), 69.5 (C$_f$), 98.80 and 98.85 (C$_g$) and 20.8 and 20.9 (C$_h$).

Example 17

1-Anilino-3,5:4,6-di-O-ethylidene-D-glucitol (Ligand 5b). A mixture of 0.38 g of 1-chloro-3,5:4,6-di-O-ethylidene-D-glucitol obtained from Example 16, 0.465 g of aniline and 0.53 g of sodium carbonate in 50 mL of acetonitrile was allowed to heat at 80° C. for 5 days. The reaction mixture was purified via silica gel chromatography (Aluminiumoxid 60 λ$_{254}$ Type E (Merck)) using chloroform as an eluent (R$_f$=0.30) to obtain 0.138 g of the above-titled compound as a viscous oil.

Example 18

1-Tosyl-3,5:4,6-di-O-ethylidene-D-glucitol. A mixture of 7.8 g of DES obtained from Example 3, 6 g of p-toluenesulfonyl chloride, 30 mL of chloroform and 30 mL of pyridine was allowed to stir at 20° C. for 2 days. The reaction mixture was purified via silica gel chromatography (Aluminiu0moxid 60 λ$_{254}$ Type E (Merck)) using chloroform as an eluent (R$_f$=0.30) to obtain 0.75 g (30%) of the above-titled compound as white crystals: mp.=101–102° C. (from Et$_2$O); $[\alpha]_D^{20}$ +4.3 (c 1, CDCl$_3$); $^1$H NMR (CDCl$_3$, 90 MHz) δ1.28 and 1.33 (d, 6H, CH$_3$), 3.50 (s, 1H, OH), 3.60 and 3.90 (m, 4H (H$_{b-e}$)), 4.08 and 4.30 (m, 4H (H$_a$ and H$_f$), 4.60–4.80 (m, 2H, H$_g$), 7.35 and 7.80 (d, 4H, Ph group); $^{13}$C NMR (CDCl$_3$, 90 MHz) δ66.54 (C$_a$) , 67.99 (C$_b$), 77.73 (C$_c$) , 69.49 (C$_d$), 69.75 (C$_e$) , 71.14 (C$_f$) , 98.57 and 98.74 (C$_g$), 20.66 and 20.85 (C$_h$). Ts group: 21.85 (CH$_3$), 128.01, 129.94, 132.46 and 145.13 (Ph).

Example 19

1-Anilino-3,5:4,6-di-O-ethylidene-D-glucitol. A mixture of 1 eq. of 1-tosyl-3,5:4,6-di-O-ethylidene-D-glucitol obtained from Example 16, 2.4 g of aniline and 2.7 g of sodium carbonate in 130 mL of acetonitrile was allowed to heat at 30° C. for 7 days. The reaction mixture was purified via silica gel chromatography (Aluminiumoxid 60 λ$_{254}$ Type E (Merck)) using chloroform as an eluent (R$_f$=0.30) to obtain 1.2 g (65.2%) of the above-titled compound which crystallized upon standing: mp.=167–168° C.; $[\alpha]_D^{20}$ +5.1 (c 1, CDCl$_3$); $^1$H NMR (CDCl$_3$, 90 MHz) δ1.39 and 1.48 (d, 6H, CH$_3$), 2.45 (br. s, 2H, OH, NH), 3.40–3.68 (m, 4H (H$_{g-f}$)), 3.70–4.30 (m, 4H (H$_{b-e}$), 4.65–4.90 (m, 2H, H$_g$), 6.72 and 7.28 (m, 5H, Ph group); $^{13}$C NMR (CDCl$_3$, 90 MHz) δ46.62 (C$_a$) , 66.68 (C$_b$) , 77.74 (C$_c$), 68.10 (C$_d$), 69.90 (C$_e$), 69.66 (C$_f$), 98.77 and 98.90 (C$_g$), 20.98 and 21.04 (C$_h$); 128.08, 129.35, 130.01 and 148.29 (Ph).

Example 20

(S)-N-isobutyl-α-phenylethylamine ((S)-IBPA). A mixture of 12.1 g (S)-phenethylamine, 15.9 g isobutyryl chloride and 14 g of KOH in 75 mL of water and 150 mL of diethyl ether was heated at 40–45° C. for several hours to afford 15.5 g (81%) of intermediate A.

A mixture of 15 g of intermediate A, 7.5 g of LAH and 60 mL of THF were heated at reflux. The reaction product was treated with 10 mL of HCl -saturated isopropanol to afford 15.4 g (92%) of the above-titled compound as white needles: mp.>200° C. (dec.); $[\alpha]_D^{20}$ −26.9 (c=4.02, MeOH); $^1$H NMR (CDCl$_3$) δ0.9–1.1 (dd, CHMe$_2$), 1.95 (d, CH$_3$CHPh), 2.2–2.4 (m, CHMe$_2$), 2.4–2.7 (m, CH$_2$), 4.2–4.4 (m, CHPh), 7.3–7.5 (m, Ph, 3H) 7.6–7.8 (Ph, 2H (ortho)), 9.4–9.8 (br. s, NH$_2^+$, 1H), 9.8–10.1 (br. s, NH$_2^+$, 1H),; $^{13}$C NMR (CDCl$_3$) δ20.20, 20.70, 20.85, 25.55 (3 CH$_3$, CHMe$_2$), 53.00, 59.50 (CH$_2$N, CHN), 127.65, 129.05, 129.20 (Ph, 4 CH), 136.15 (Ph, C—CH).

Example 21

(R)-N-isobutyl-α-phenylethylamine ((R)-IBPA). (R)-IPBA was obtained according to the synthesis of (S)-IBPA in Example 20, except that (R)-phenethylamine was used in place of (S)-phenethylamine.

Example 22

(S,S)-N,N-Bis(methylbenzyl)ethylenediamine ((S,S)-BMBE). A mixture of 36.7 g of (S)-phenethylamine and 22 mL of diethyloxalate was allowed to warm to 40° C. over 30 min. The reaction mixture was diluted with 600 mL of THF, treated with 34 g of LAH, and allowed to heat at reflux for 10 h to afford, following distillation, 15.3 g (38%) of the above-titled compound: bp. 170° C./1 torr; $[\alpha]_D^{18}$ −70.7 (neat) (lit. $[\alpha]_D^{25}$ −65.6 (Tetrahedron Lett., 1980, 3467)); $^1$H NMR (CDCl$_3$) δ1.4 (d, CH$_3$), 1.65 (br. s, NH), 2.6 (s, CH$_2$CH$_2$), 3.7 (q, CH), 7.2–7.4 (m, arom.).

Example 23

1,2:3,5-Di-O-isopropylidene-α-D-xylofuranose (DIXF). A mixture of 33 g of D-xylose, 667 mL of acetone, 3.3 mL of conc. sulfuric acid and 66.7 g of CuSO$_4$ were allowed to stir at room temperature for 25 h. Distillation (110–1130 C/1 torr) of the reaction mixture afforded 42 g (89%) of the above-titled compound (lit. (J. Am. Chem. Soc., 1955, 77, 5900) 90–92° C./0.2 torr).

Example 24

1,2-O-isopropylidene-α-D-xylofuranose (IXF, Ligand 10). Ligand 10 was prepared according to the procedure described in J. Am. Chem. Soc., 1955, 77, 5900. 13.5 g of DIXF obtained from Example 23 and 60 mL of 0.2% HCl were heated for 1 h with intensive stirring to afford 9.6 g (86%) of the above-titled compound: $[\alpha]_D^{25}$=−17° (c 2.1, MeOH) (lit. (Ber., 1923, 56, 863) $[\alpha]_D^{25}=-19°$ (c 0.7, MeOH)); $^1$H NMR (CDCl$_3$) δ1.21 and 1.36 (2s, Me$_2$C), 3.6 (s, 2 OH), 3.86 (d, CH$_2$), 3.82–4.42 (m, 1 CH$_2$O, 3 CHO), 5.86 (d, OCHO); $_{13}$C NMR (CDCl$_3$) δ111.42, 104.48, 85.18, 79.26, 77.0, 75.62, 66.72, 60.22.

Example 25

(R)-1-tert-Butylamino-2,3-propanediol (BAP). BAP was obtained according to the procedure of Example 9, above.

Example 26

1,2-O-Cyclohexylidene-α-D-xylofuranose (CXF). CXF was obtained according to the method described in J. Org. Chem. 1965, 30(4), 1288. A mixture of 9.5 g of D-xylose, 100 mL of cyclohexanone and catalytic sulfuric acid was allowed to stir at room temperature for approximately 25 h to afford, following recrystallization, 10.05 g (50%) of 1,2:3,5-di-α-D-xylofuranose (DCXF): mp.=101–102° C. (lit. 103–104° C.).

5 g of DCXF obtained above were allowed to stir in 150 mL of 60% aqueous acetic acid at 20° C. for 20 h to obtain, following recrystallization, the above-titled compound: mp.=84–85 (lit. 83–84).

Example 27

(S)-Phenylalaninol ((S)-PA). (S)-PA was prepared according to the method described in Tetrahedron Lett., 1992, 33, 5517. 5 g of (S)-phenylalanine were treated with 2 g of sodium borohydride and 2 mL of H$_2$SO$_4$ in 30 mL of THF, maintaining the reaction temperature below 10° C. The reaction mixture was allowed to stir at this temperature for 3 h, then at 30° C. for 12 h. The resulting mixture was treated was 30 mL of NaOH and was heated at just below 100° C. for 3 h to afford 4 g of the above-titled compound: mp.= 94–95° C.; $[\alpha]_D^{20}=-21$ (c=2, MeOH) (lit. 95° C.; $[\alpha]_D^{20}=-23.3$ (c=2, MeOH) (Indian J. Chem., 1966, 4, 177)).

Example 28

(S)-N,N-(Dimethyl)phenylalaninol [(S)-DMPA]. (S)-DMPA was synthesized according to the method described in J. Chem. Soc., 1950, 1342; and J. Am. Chem. Soc., 1970, 92, 2476. The structure of the above-titled compound is consistent with $^1$H and $^{13}$C NMR data.

Example 29

(3S,4S)-1-Benzyl-3,4-dihydroxypyrrolidine (BDHP). BDHP was obtained according to the method described in Ber., 1986, 199, 3326 and in Chem. Phar. Bull., 1991, 39, 2219. A mixture of 15 g of L-tartaric acid and 1.9 mL of benzylamine in xylene was heated at reflux for 7 h to afford, after crystallization, 11 g (52%) of an N-benzylimide intermediate: mp.=199–201° C. (lit. 196–98° C., Can. J. Chem. 1968, 46, 3091); $[\alpha]_D^{23}=+138$ (c=1, MeOH) (lit. $[\alpha]_D^{23}=+138$ (c=1, MeOH), Chem. Phar. Bull., 1991, 39, 2219).

The N-benzylimide intermediate obtained above was added to a suspension of LAH in THF with stirring, under argon, at 0° C. The resulting mixture was heated at reflux for 12 h to provide 5.1 g (53%) of the above-titled compound: mp.=99–100° C. (lit. 109–110° C.); $[\alpha]_D^{20}=+8.1$ (c=1, CHCl$_3$) (lit. $[\alpha]_D^{20}=+8.3$ (c=1, CHCl$_3$)).

Example 30

1-O-Triphenylmethyl-3,5:4,6-di-O-ethylidene-D-glucitol (TDG). A mixture of 11.7 g of DES obtained from Example 3, 16.3 g of triphenylmethyl chloride and 80 mL of pyridine were allowed to stir at room temperature for 3 days, to afford, following crystallization from 10:1 hexane:benzene, 15.3 g (64%) of the above-titled compound: mp.=92° C. (MeOH); $^{13}$C NMR data consistent with that reported in M. I. Struchkova et al., Izv. Akad. Nauk. Ser. Khim., 1989, 2492.

Example 31

1,3:4,6-Di-O-(ρ-anisylidene)-D-mannitol (DAM). A mixture of 20 g of D-mannitol, 26 mL of p-anisaldehyde in 60 mL of dimethylformamide was treated with 4 mL of sulfuric acid added in one portion. The resulting mixture was allowed to stand at room temperature for 72 h and then poured into a mixture of 12 g of potassium carbonate and 0.6 L of ice water. The unreacted ρ-anisaldehyde was extracted in hexane and 1:1 hexane:benzene. The resulting aqueous layer was allowed to stand at 5–10° C. whereupon a white, cheese-like solid deposited thereon. The aqueous layer was filtered, and the solid air-dried and recrystallized from 6:1 benzene:ethanol to afford 4.3 g (11%) of the above-titled compound. The above-titled compound was dried over P$_2$O$_5$ in an Abderhalden apparatus for 18 h at 40° C. (CH$_2$Cl$_2$) under reduced pressure to provide an analytical specimen melting at 186–88° C.: $[\alpha]_D^{16}$ 24° (c=1 , acetone); $^1$H NMR (200 MHz, DMSO-d$_6$) δ3.5 (dd, 2H, H-2 and H-5), 3.73 (s, 6H, OMe), 3.8 (m, 4H, H-1 and H-6), 4.15 (dd, 2H, H-3 and H-4), 5.32 (d) and 5.48 (s, OH, and PhCH), 6.9 (d) and 7.35 (d, 8H, Ph); $^{13}$C (50 MHz, DMSO-d$_6$) δ55.11 (OMe), 58.66 (C-2, C-5), 70.97 (C-1, C-6), 78.05 (C-3 and C-4), 100.1 (C-7, C-8), 113.30, 127.44, 130.68 and 159.37 (Ph).

Example 32

1,3:4,6-Di-O-(ρ-toluylidene)-D-mannitol (DTM1). A mixture of 20 g of D-mannitol, 26 mL of ρ-toluylaldehyde in 60 mL of dimethylformamide was treated with 4 mL of sulfuric acid added in one portion. The resulting mixture was allowed to stand at room temperature for 72 h and then poured into a mixture of 12 g of potassium carbonate and 0.6 L of ice water. The unreacted ρ-toluylaldehyde was extracted in hexane. The resulting aqueous layer was allowed to stand at 5–10° C. whereupon a white, cheese-like solid deposited thereon. The aqueous layer was filtered, and the solid air-dried and recrystallized from 6:1 benzene:ethanol to afford 13.8 g (32.5%) of the above-titled compound. The above-titled compound was dried over P$_2$O$_5$ in an Abderhalden apparatus for 18 h at 40° C. (CH$_2$Cl$_2$) under reduced pressure to provide an analytical specimen melting at 156–58° C.: $[\alpha]_D^{16}$ 11° (c=0.5, acetone); $^1$H NMR (200 MHz, DMSO-d$_6$) δ2.3 (s, 6H, CH$_3$Ph), 3.5 (dd, 2H, H-2 and H-5), 3.8 (m, 4H, H-1 and H-6), 4.15 (dd, 2H, H-3 and H-4), 5.32 (d) and 5.48 (s, OH, and PhCH), 7.16 (d) and 7.32 (d, 8H, Ph); $^{13}$C (50 MHz, DMSO-d$_6$) δ20.81 (MePh), 58.66 (C-2, C-5), 71.10 (C-1, C-6), 78.10 (C-3 and C-4), 100.25 (C-7, C-8), 126.04, 128.46, 135.50 and 137.76 (Ph).

Example 33

2,3-O-Cyclohexylidene-1,1,4,4-tetraphenyl-L-threitol (CYTOL). A solution of 25 g of dimethyl-L-tartrate and 0.9 g of p-TsOH in 225 mL of abs. benzene was heated at reflux, and to it was added 15 mL of freshly distilled cyclohexanone over a period of 30 minutes. The resulting solution was heated for 8 h and the water thus produced was continuously removed via a Dean-Stark apparatus. After cooling to room temperature, the reaction mixture was diluted with 200 mL of diethyl ether and the resulting mixture was washed three times with 200 mL water and 200 mL of brine, and dried over MgSO$_4$. Concentration afforded 28 mL of an oil, which was subsequently diluted with 15 mL of 1:1 ether:hexane and chromatographed on silica gel using a 20×2 cm column and 1:1 ether:hexane eluent to provide 28.6 g (79%) dimethyl-2,3-O-cyclohexylidene-L-tartrate as a light, yellow oil, which was approximately 90% pure, and was used in the next step without further purification.

A diethyl ether solution (300 mL) of phenylmagnesium bromide obtained from the reaction of 50 mL of bromobenzene and 11.6 g of magnesium was added dropwise with stirring to a diethyl ether solution (130 mL) of the 28.6 g of dimethyl-2,3-O-cyclohexylidene-L-tartrate obtained above at 3–5° C. over 4.5 h. The resulting mixture was heated at reflux for 2 h, allowed to cool to room temperature, and poured onto ice-water (approx. –5° C.) containing NH$_4$Cl. The resulting organic layer was washed with 10% HCl (10 mL) and water, and then dried over MgSO$_4$. Evaporation of the solvent provided allowed the product to crystallize to afford 17 g (34%) of the above-titled compound: mp.= 200–202° C. (lit. 195–196° C.; Helv. Chim. Acta, 1987, 70, 954); $^1$H NMR (CDCl$_3$) δ1.2–1.6 (m, 5H), 4.65 (c, 2CH), 4.77 (c, 2OH), 7.3–7.6 (m, 20 CH aromatic).

Example 34

Di-O-cyclohexylidene-D-allofuranose (DCAF). 45 g of D-glucose were added to a mixture of 10 mL of cyclohexanone and 0.7 mL of sulfuric acid. The resulting mixture was allowed to stir at 20–22° C. for 12 h, forming a suspension. 25 mL of heptane were added, and the resulting mixture was allowed to stir at 55–60° C. until two separate liquid layer formed and dissolved the suspension. The upper heptane layer was decanted, and the dark, lower layer was cooled and stored in a refrigerator at 4° C. The crude, solid product that formed after approximately 10 h was filtered and recrystallized from toluene and then from hexane to give 3.7 g (43%) of 1,2:5,6-di-O-cyclohexylidene-D-glucofuranose: mp.= 130–131.5° C. (lit. 131–132.5, R. C. Hockett et al., J. Am. Chem. Soc., 1949, 71, 3072).

1.0 g of 1,2:5,6-di-O-cyclohexylidene-D-glucofuranose obtained above was added to a reaction vessel containing a mixture of 2.0 mL of acetic anhydride and 8.0 mL of dimethylsulfoxide preheated at 70° C. The reaction vessel was quickly stoppered and heated at 70° C. in a water bath for 75 min. After cooling to room temperature, the reaction mixture was concentrated in vacuo at 70° C./2 torr to give crude ketone as a syrup, which was used in the next step without further purification.

0.85 g of the crude ketone obtained above was dissolved in 6 mL of 96% aqueous ethanol. The resulting solution was cooled to 0° C. and treated with 0.07 g of NaBH$_4$ in one portion with vigorous magnetic stirring. The resulting mixture was allowed to stir at 0° C. for 10 min, and at room temperature for 1 h. The reaction mixture was concentrated in vacuo, diluted with water (3 mL), and extracted with CHCl$_3$ (3×15 mL). The extract was washed with water, dried (Na$_2$SO$_4$) and concentrated in vacuo. The resulting solidified syrup was recrystallized from diethyl ether-hexane to afford 0.35 g (35%) of the above-titled compound: rap.= 127–28° C.; $^1$H NMR (CDCl$_3$) δ1.40–1.80 (m, 10H), 2.65 (d, 1H J=2.5 Hz, OH), 3.95–4.45 (m, 5H, 6-H$_2$, 5-H, 4-H, 3-H), 4.55 (d, 1H, J=3 Hz, 2-H), 5.95 (d, 1H, J=3 Hz, 1-H).

Example 35

Di-O-isopropylidene-D-allofuranose (DIPAF). 25 g of D-glucose were added to a mixture of 600 mL of acetone and 24 mL of sulfuric acid pre-cooled to 0–5° C. The resulting suspension was allowed to stir at room temperature for 10 h. A stream of gaseous NH$_3$ was added at 0–10° C. forming (NH4)$_2$SO$_4$, which was removed by filtration. The filtrate was diluted with 30 mL of 0.1 N ammonium hydroxide, and the resulting mixture was concentrated in vacuo. The resulting residue was diluted with water (100 mL) and extracted with CHCl$_3$ (3×15 mL). Combined CHCl$_3$ extracts were washed with water, dried (Na$_2$SO$_4$) and evaporated, and the resulting residue was dissolved in benzene. The benzene solution was warmed to 65–70° C. and diluted with 45 mL of hot hexane. Crystals deposited upon standing at room temperature. Recrystallization from 1:4 benzene:hexane afforded 1,2:5,6-di-O-isopropylidene-D-glucofuranose: mp.=109–110° C.; $[\alpha]_D^{20}$ –18°.

5.0 g of 1,2:5,6-di-O-isopropylidene-D-glucofuranose obtained above was added in one portion to a reaction vessel containing a mixture of 10 mL of acetic anhydride and 40 mL of dimethylsulfoxide preheated at 70° C. The reaction vessel was quickly stoppered and heated at 70° C. in a water bath for 75 min. After cooling to room temperature, the reaction mixture was concentrated in vacuo at 70° C./2 torr to give crude ketone as an oil, which was used in the next step without further purification.

2 g of the crude ketone obtained above was dissolved in 30 mL of 96% aqueous ethanol. The resulting solution was cooled to 0° C. and treated with 0.120 g of NaBH$_4$ in one portion. The resulting mixture was allowed to stir at 0° C. for 10 min, and then at room temperature for 1 h. The reaction mixture was concentrated in vacuo, and shaken with a mixture of water (15 mL) and CHCl$_3$ (5 mL). The aqueous layer was separated and extracted with CHCl$_3$ (2×5 mL). Combined organic extracts were washed with water, dried (Na$_2$SO$_4$) and concentrated in vacuo to afford a syrup. The syrup was dissolved in 3 mL of benzene, heated to 65–70° C., diluted with 12 mL of hot hexane and left to stand at room temperature overnight. The resulting crystalline precipitate was recrystallized from 1:4 benzene:hexane to afford 0.9 g (45%) of the above-titled compound: mp.= 77–78° C. (lit. 77–78° C., O. Theander, Acta Chem, Scand., 1964, 18, 2209); $^1$H NMR (CDCl$_3$) δ1.36 (s, 3H), 1.41 (s, 3H), 1.47 (s, 3H), 1.50 (s, 3H), 2.50 (br. s, 1H, OH), 3.60–4.45 (m, 5H, 6-H$_2$, 5-H, 4-H, 3-H), 4.65 (d, 1H, J=3 Hz, 2-H), 5.83 (d, 1H, J=3 Hz, 1-H).

Example 36

2,3:4,6-Di-O-isopropylidene-L-sorbofuranose (DIPS). 24 mL of sulfuric acid were added dropwise, with vigorous stirring, to 100 mL of acetone cooled to 0–5° C., at a rate such that the reaction temperature remained below 20° C. 5 g of L-sorbose were added to the reaction mixture, and stirring was allowed to continue for 4 h at room temperature. The reaction mixture was allowed to stand at room temperature overnight, and was cooled to –8° C. (ice-NaCl bath). The cooled reaction mixture was neutralized to pH 8 with saturated NaHCO$_3$ at a rate such that the reaction temperature remained below 0° C. The resulting mixture containing precipitated Na$_2$SO$_4$ was allowed to warm to room temperature and the Na$_2$SO$_4$ was filtered and washed twice with dry acetone. Combined organic filtrate and washings were concentrated in vacuo at 20° C., and the resulting oily residue was extracted with chloroform (5×10 mL). The chloroform extract was dried (MgSO$_4$) and evaporated to afford a viscous gum which crystallized (mp.=59–61° C.) upon standing. Recrystallization (benzene) of the above crystallized gum afforded 4.8 g (67%) of the above-titled compound as fine crystals: mp.=76–77° C. (lit. 77–78° C. (T.

Reichstein et al., Helv. Chim. Acta, 1934, 17, 331); $^1$H NMR (CDCl$_3$) δ1.35 (s, 6H), 1.45 (s, 3H), 1.52 (s, 3H), 2.50 (br. s, 1H, OH), 3.75–3.90 (m, 2H, 6-H$_2$), 4.05–4.15 (m, 3H), 4.33 (d, 1H, 3H), 4.5 (d, 1H, J≈1H, 1-H).

Example 37

(−)-8-Methoxy-trans-p-menth-3-ol (MTM). A mixture of 1.54 g of (−)-isopulegol (Fluka Chemical Corporation, Ronkonkoma, N.Y.), 1.13 g of acetic anhydride and 3 mL of pyridine were allowed to stir at room temperature for 12 h. The resulting mixture was concentrated at 60° C./20 torr, and the resulting residue was dissolved in diethyl ether. The ether solution was washed with dilute HCl, aqueous NaHCO$_3$, and water, and then dried (MgSO$_4$) and concentrated to provide (−)-isopulegol acetate as a colorless oil: IR (ν/cm$^{-1}$, CCl$_4$) 3040, 1740, 1665, 9052.

A solution of 1.78 g of (−)-isopulegol acetate obtained above in 30 mL of MeOH was cooled to 0° C., and to it was added 3.2 g of Hg(OAc)$_2$. After 3 h, 15 mL of 3M NaOH were added, followed by 15 mL of 0.5M NaBH$_4$ in 3M NaOH. The resulting mixture was concentrated at 40° C./20 torr. The resulting residue was dissolved in diethyl ether, washed with water, dried (MgSO$_4$) and concentrated to provide a crude product, which was chromatographed on silica gel using hexane and 4:1 hexane:diethyl ether to provide 1.34 g (72%) of the above-titled compound: R$_f$ 1:9 EtOAc:heptane=0.18; IR (ν/cm$^{-1}$, CCl$_4$) 3600–3200, 3040–2760, 1450, 1385, 1370, 1150, 1052; $^1$H NMR (300 MHz, CDCl$_3$) δ0.9 (d, 3H, 5-Me), 0.93 (m, 3H), 1.16 and 1.20 (s, 6H, CMe$_2$), 1.43 (m, 2H), 1.63 (m, 2H), 1.96 (dm, 1H, 2-H), 3.24 (s, 3H, OMe), 3.62 (ddd, 1H, 1-H), 5.15 (br. s, 1H, OH); $^{13}$C NMR (75.5 MHz, CDCl$_3$) δ19.65, 21.83 and 23.36 (CH$_3$), 26.46 (CH$_2$), 30.77 (CH), 34.49 (CH$_2$), 43.72 (CH$_2$), 48.27 (OCH$_3$), 50.05 (CH), 71.77 (CH), 80.40 (C).

Example 38

1,2:3,5-Di-O-benzylidene-D-glucofuranose (DBGLU). A mixture of powdered 10 g of D-glucose, 20 g of anhydrous, freshly fused ZnCl$_2$, 60 mL of benzaldehyde and 7.7 mL of glacial acetic acid was shaken at room temperature for 17 h. The resulting light straw-colored solution was poured into 200 mL of ice water, extracted with ether (3×100 mL), washed with aqueous NaHCO$_3$, dried (Na$_2$SO$_4$), treated with 1 g of decolorizing carbon, and filtered. The filtrate was concentrated (70° C./1 mm) and purified using silica gel chromatography (benzene, then 4:1 benzene:ether) to afford a pure product (R$_f$=0.3 (4:1 benzene:ether)) which was recrystallized from 2:1 benzene:ethyl acetate to afford 1.38 g (7%) of the above-titled compound: mp.=160–61° C.; [α]$_D^{20}$ 40° (c 1.0, CHCl$_3$; identical with literature values, J. Am. Chem. Soc. 1957, 79, 3862); $^1$H NMR spectrum identical with that described in Carbohydrate Research, 1968, 8, 125.

Example 39

L-(−)-2,4:3,5-Di-O-methylidene-D-xylitol (L-DMX). Xylitol (Fluka Chemical Corporation, Ronkonkoma, N.Y.) was converted to DL-2,4:3,5-di-O-methylidenexylitol according to the procedure of R. M. Hann et al., J. Am. Chem. Soc., 1944, 66, 670 in 65% yield: mp.=201–202° C. (5:1 EtOH:H$_2$O; lit. 201–202° C. (R. M. Hann et al., J. Am. Chem. Soc., 1944, 66, 670)); $^1$H NMR (CDCl$_3$) δ1.36 (br. s, 1H, OH), 3.55–3.95 (7H, 1-H$_2$, 5-H$_2$, 2-H, 3-H, 4-H), 4.75 (ddd, 2H, AB-system, OCH$_2$O), 5.20 (ddd, 2H, AB-system, OCH$_2$O).

A mixture of 4.4 g of the DL-2,4:3,5-di-O-methylidenexylitol obtained above, 3.06 g of acetic anhydride and 5 mL of pyridine were allowed to mechanically stir at 20 . 22° C. for 3 h, whereupon crystalline acetate product began to precipitate. Stirring continued for an additional 3 h, whereupon the resulting crystals were filtered, washed with water, and recrystallized from methanol. Aqueous washings were combined with the original mother liquor, concentrated in vacuo and recrystallized from methanol to provide DL-1-O-acetyl-2,4:3,5-di-o-methylidenexylitol in a combined yield of 81.5%: mp.= 154–55° C. (lit. 156–57° C. (R. M. Hann et al., J. Am. Chem. Soc., 1944, 66, 670)); $^1$H NMR (CDCl$_3$) δ2.10 (s, 3H), 3.6 (d) and 3.85 (dd, 2H, AB-system, J$_{AB}$=15 Hz, J=2 Hz, 5-H$_2$) overlapped with 3.90 (m, 1H, J=2 Hz, 4-H), 4.15–4.45 (m, 4H, 2-H, 3-H, 1-H$_2$), 4.75 (d, 2H, AB-pattern, —OCH$_2$O—), 5.15 and 5.25 (d, 2H, AB-pattern, —OCH$_2$O—).

To a magnetically stirred suspension of porcine pancreatic lipase (specific activity =47.8 U/mg; Olainfarm, Latvia) in 6 mL of 0.1M phosphate buffer, was added 0.327 g of DL-1-O-acetyl-2,4:3,5-di-O-methylidenexylitol obtained above. The resulting mixture was allowed to stir at 20–22° C. for 24 h in a stoppered flask and under an atmosphere of argon. The reaction mixture was diluted with water (4 mL), and extracted with chloroform (10 mL). The aqueous layer containing the above-titled compound was set aside, and the chloroform layer containing D-(+)-O-acetyl-2,4:3,5-di-O-methylidenexylitol was concentrated. The residue from the concentration of the chloroform layer was recrystallized from MeOH to provide D-(+)-O-acetyl-2,4:3,5-di-O-methylidenexylitol in 95% yield: mp.=154–55° C.; [α]$_D^{20}$ +2.50 (c=0.5, CHCl$_3$).

The above-mentioned aqueous layer was filtered through a pad of Celite, concentrated in vacuo (45° C.), diluted with MeOH (10 mL) and filtered. The resulting filtrate was diluted with 2 mL of diethyl ether to afford 123 mg (93%) of the above-titled compound as white, silky crystals: mp.= 214–17° C.; [α]$_D^{20}$ −25.70 (c=0.54, water) (lit. 217–19° C.; [α]$_D^{20}$ −25.30 (water) (R. M. Hann et al., J. Am. Chem. Soc., 1944, 66, 670)); $^1$H NMR indistinguishable from that obtained for DL-2,4:3,5-di-O-methylidenexylitol, above.

Example 40

D-(+)-2,4:3,5-Di-O-methylidene-D-xylitol (D-DMX). To a stirred solution of 0.084 g of KOH in 10 mL of 1:1 MeOH:H$_2$O were added, in one portion, 0.218 g of D-(+)-O-acetyl-2,4:3,5-di-O-methylidenexylitol obtained according to the procedure of Example 39, above. The resulting mixture was allowed to stir at 22–23° C. for 2.5 h, whereupon the mixture was concentrated in vacuo to approximately half its volume, and extracted with CHCl$_3$ (3 mL). The resulting aqueous phase was evaporated, and the resulted solid residue was treated with 10 mL of dry methanol, filtered and concentrated. This step was repeated several times to provide a clear solution from which crystals of the above-titled compound were obtained upon the gradual addition of Et$_2$O. Recrystallization from EtOH afforded 0.114 g (65%) of the above-titled compound: mp.=213–16° C.; [α]$_D^{20}$ +23.0° (c=0.25, water). Additional recrystallization from EtOH provided a substantially pure specimen: [α]$_D^{20}$ +25.20 (c=0.30, water; lit. (L-enantiomer) [α]$_D^{20}$ −25.30 (water)).

Example 41

(S)-(−)-α,α-Diphenyl-(1,2,3,4-tetrahydroisoquinolin-3-yl)-methanol (DTM2). A mixture of 1 eq. of (S)-1,2,3,4- tetrahydro-3-isoquinolinecarboxylic acid (Aldrich Chemical Co., Milwaukee, Wis.), 5 eq. of trimethylorthoformate, methanol and catalytic HCl were allowed to heat at reflux for 5 h. Concentration in vacuo provided methyl (S)-1,2,3,4-tetrahydro-3-isoquinolinecarboxylate.

(S)-1,2,3,4-tetrahydro-3-isoquinolinecarboxylate obtained by the procedure above was treated with 2 eq. of phenylmagnesium bromide according to the procedure of Example 33, to obtain the above-titled compound.

CHIRAL HYDRIDE COMPLEXES SYNTHESIZED

Materials and Methods

Tetrahydrofuran (THF) was dried over NaOH, passed twice through columns of freshly preheated (300° C.) neutral alumina, dried over metallic sodium (2 days) and distilled over calcium hydride. Sodium aluminum hydride (Cambrex Co.) was dissolved in THF at reflux under an argon atmosphere for 10 h until no $H_2$ evolved and decanted into a well stoppered vessel.

Example 42

NaAlH(DIPM)(OMe). A mixture of a 30 mL solution (THF) of 2.46 g of DIPM obtained above in Example 2, and a solution of 8.48 mmol of sodium aluminum hydride in 30 mL of THF was cooled to 0° C. for 1 h, whereupon 0.34 mL of MeOH were added, providing a homogeneous reaction mixture of the above-titled complex after 1 h.

Example 43

NaAlH(Ligand 3). A mixture of 0.259 g of Ligand 3 obtained above from Example 9 and 0.054 g of sodium aluminum hydride in 5 mL of toluene was heated gradually to 100° C. and stirred at that temperature until hydrogen evolution ceased (approx. 2 h). The resulting pale yellow solution of the above-titled complex was filtered off and titrated with MeOH, providing 21.5 cm$^3$ of hydrogen.

Example 44

NaAlH((S)-PROP). A mixture of 0.259 g of ((S)-PROP) obtained above from Example 9 and 0.108 g of sodium aluminum hydride in 5 mL of toluene was heated gradually to 100° C. and stirred at that temperature until hydrogen evolution ceased (approx. 2 h). The resulting pale yellow solution of the above-titled complex was filtered off and titrated with MeOH, providing 20 cm$^3$ of hydrogen.

Example 45

NaAlH[(S)-BINOL](OMe). A mixture of 0.239 g of sodium aluminum hydride and 0.17 mL of MeOH in 10 mL of THF was allowed to stir at room temperature for 20 min. A 12 mL solution (THF) of 1.21 g of (S)-Binol obtained from Example 8 was added, and the resulting mixture was allowed to stir at room temperature for over 40 min affording a THF solution of the above-titled complex.

Example 46

NaAlH$_2$(DES). A mixture of 0.9 g of DES obtained from Example 3 in 150 mL of THF and 3.9 mmol of sodium aluminum hydride in 15 mL of THF were allowed to stir at 0° C. for 20 minutes to afford a THF solution of the above-titled complex.

Example 47

NaAlH(DES)(OMe). A solution of 0.083 g of MeOH in 20 mL of THF was added to 2.6 mmol of sodium aluminum hydride in 10 mL of THF at 0° C. for 1 h. A solution of 0.6 g of DES obtained from Example 3 in 100 mL of THF was added to the above solution over 1 h, and the resulting solution was allowed to stir at 0° C. for 20 min., affording a THF solution of the above-titled complex.

Example 48

NaAlH$_2$(BCG). A mixture of 0.23 g of sodium aluminum hydride in 15 mL of THF and 1.49 g of BCG obtained from Example 12 in 20 mL of THF were allowed to stir at 0° C. for 30 min. to afford a THF solution of the above-titled complex.

Example 49

NaAlH(BCG)(OMe). A mixture of 0.088 g of MeOH in 7 mL of THF and 0.148 g of sodium aluminum hydride in 9.7 mL of THF was allowed to stir at 0° C. for 5 min. To the resulting solution was added 0.96 g of BCG obtained from Example 12 in 27 mL of THF. The resulting solution was allowed to stir at 0° C. for 20 min. to afford a THF solution of the above-titled complex.

Example 50

NaAlH$_2$(DCG)$_2$. To 0.153 g of sodium aluminum hydride in 10 mL of THF was added 1.93 g of DCG obtained from Example 10 in 20 mL of THF. The resulting solution was allowed to stir at 0° C. for 25 min. to afford a THF solution of the above-titled complex.

Example 51

NaAlH(DCG)$_2$(OMe). To 0.229 g of sodium aluminum hydride in 15 mL of THF was added 0.108 g of MeOH in 17 mL of THF. The resulting solution was allowed to stir at 0° C. for 5 min. To the resulting solution was added 2.89 g of DCG obtained from Example 10 in 30 mL of THF. The resulting solution was allowed to stir at 0° C. for 15 min. to afford a THF solution of the above-titled complex.

Example 52

NaAlH(DCG)$_3$. To 0.153 g of sodium aluminum hydride in 10 mL of THF was added 2.89 g of DCG obtained according to the procedure of Example 10 in 40 mL of THF. The resulting solution was allowed to stir at 0° C. for 40 min. to afford a THF solution of the above-titled complex.

Example 53

NaAlH(Eph)(OMe). To 0.420 g of sodium aluminum hydride in 27.5 mL of THF was added 0.256 g of MeOH in 5 mL of THF. The resulting solution was allowed to stir at 0° C. for 5 min. To the resulting solution was added 1.32 g of (1R,2S)-(−)-ephedrine ("Eph") (Aldrich Chemical Co., Milwaukee, Wis.) in 25 mL of THF. The resulting solution was allowed to stir at 0° C. for 10 min. to afford a THF solution of the above-titled complex.

Example 54

NaAlH$_2$(DBM)$_2$. To 0.32 mmol of sodium aluminum hydride in 1 mL of THF was added 0.115 g of DBM obtained from the procedure of Example 14 in 1.8 mL of THF. The resulting solution was allowed to stir at 25° C. for 20 min. to afford a THF solution of the above-titled complex.

Example 55

NaAlH$_2$[(S)-BINOL]. A mixture of 1.57 g of sodium aluminum hydride and a 5 mL solution (THF) of 0.582 g of (S)-binol obtained from Example 8 was added, and the resulting mixture was allowed to stir at 21° C. for 15 min affording a THF solution of the above-titled complex.

Example 56

NaAlH[(S)-BINOL](OEt). A mixture of 1.57 g of sodium aluminum hydride and 1.42 g of EtOH in 10 mL of THF was allowed to stir at room temperature for 20 min. A 5 mL solution (THF) of 0.582 g of (S)-Binol obtained from Example 8 was added, and the resulting mixture was allowed to stir at 21° C. for 15 min affording a THF solution of the above-titled complex.

Example 57

NaAlH(DIPM)(2-NfOH). A mixture of 0.153 g of sodium aluminum hydride in 10 mL of THF and 0.74 g of DIPM obtained above in Example 2 in 20 mL of THF was allowed to stir at 0° C. for 15 min. A 20 mL solution (THF) of 0.41 g of 2-naphthol (2-NfOH) was added, and the resulting mixture was allowed to stir at 0° C. for 15 min affording a THF solution of the above-titled complex.

Example 58

NaAlH(DCG)(2-NfOH)$_2$. A mixture of 0.136 g of sodium aluminum hydride in 9 mL of THF and 0.86 g of DCG obtained according to the procedure of Example 10 in 20 mL of THF was allowed to stir at 0° C. for 15 min. A 20 mL solution (THF) of 0.73 g of 2-naphthol (2-NfOH) was added, and the resulting mixture was allowed to stir at 0° C. for 15 min affording a THF solution of the above-titled complex.

Example 59

NaAlH(AG). A mixture of 0.153 g of sodium aluminum hydride in 10 mL of THF and 0.458 g of 1,6-anhydro-β-D-glucose ("AG") (Aldrich Chemical Co., Milwaukee, Wis.) in 30 mL of THF was allowed to stir at 0° C. for 15 min. affording a THF solution of the above-titled complex.

Example 60

NaAlH[(S,S)-BPAP]. A mixture of 0.142 g of sodium aluminum hydride and 0.86 g of (S,S)-BPAP obtained according to the procedure of Example 15 in 5 mL of THF was allowed to stir at room temperature for 15 min. affording a THF solution of the above-titled complex.

Example 61

NaAlH(DBM)(iso-Bu). To 0.140 g of sodium aluminum hydride in 10 mL of THF was added 0.93 g of DBM obtained from the procedure of Example 14 in 50 mL of THF. To the resulting solution was added 0.19 g of isobutyl alcohol (iso-Bu) in 20 mL of THF. The resulting solution was allowed to stir at 24° C. for 20 minutes to afford a THF solution of the above-titled complex.

Example 62

NaAlH(DIPM)[(S)-IBPA]. A mixture of 0.066 g of sodium aluminum hydride in 5 mL of THF and 0.32 g of DIPM obtained above in Example 2 in 10 mL of THF was allowed to stir at 0° C. for 15 min. A 10 mL solution (THF) of 0.216 g of (S)-IBPA obtained according to the procedure of Example 20 was added, and the resulting mixture was allowed to stir at 0° C. for 15 min affording a THF solution of the above-titled complex.

Example 63

NaAlH(DIPM)[(R)-IBPA]. A mixture of 0.066 g of sodium aluminum hydride in 5 mL of THF and 0.32 g of DIPM obtained above in Example 2 in 10 mL of THF was allowed to stir at 0° C. for 15 min. A 10 mL solution (THF) of 0.216 g of (S)-IBPA obtained according to the procedure of Example 21 was added, and the resulting mixture was allowed to stir at 0° C. for 15 min affording a THF solution of the above-titled complex.

Example 64

NaAlH$_2$(BDG)$_2$. A mixture of 0.140 g of sodium aluminum hydride in 10 mL of THF and 1.68 g of BDG obtained above in Example 13 in 100 mL of THF was allowed to stir at 20° C. for 20 minutes affording a THF solution of the above-titled complex.

Example 65

NaAlH[(S,S)-BMBE](OMe). A mixture of 0.0716 g of sodium aluminum hydride in 5 mL of THF and 0.356 g of (S,S)-BMBE obtained according to the procedure of Example 22 in 10 mL of THF was allowed to stir at 20° C. for 1 h. A 5 mL solution (THF) of 0.0424 g of MeOH was added, and the resulting mixture was allowed to stir at room temperature for 20 min. affording a THF solution of the above-titled complex.

Example 66

NaAlH$_2$(DIPM). A mixture of 0.0716 g of sodium aluminum hydride in 5 mL of THF and 0.35 g of DIPM obtained according to the procedure of Example 2 in 15 mL of THF was allowed to stir at 0° C. for 10 min. affording a THF solution of the above-titled complex.

Example 67

NaAlH2[(S)-IBPA]$_2$. A mixture of 0.0716 g of sodium aluminum hydride in 5 mL of THF and 0.705 g of (S)-IBPA obtained according to the procedure of Example 20 in 15 mL of THF was allowed to stir at 30° C. for 85 min. affording a THF solution of the above-titled complex.

Example 68

[NaAlH(OEt) ((S)-PEA)]$_n$. 6.53 mL of a 0.306 M solution of NaAlH$_3$(OEt) in THF was added dropwise to 2 mL of a 1 M solution (THF) of (S)-α-phenylethylamine ("(S)-PEA") (Zeeland Chemicals, Zeeland, Mich.) at 20° C. and was allowed to stir for 1 h affording a THF solution of the above-titled complex.

Example 69

Na$_2${[AlH$_2$(OEt)]$_2$[(S)-PEA]}. 6.53 mL of a 0.306 M solution of NaAlH$_3$(OEt) in THF was added dropwise to 1 mL of a 1 M solution (THF) of (S)-α-phenylethylamine ("(S)-PEA") (Zeeland Chemicals, Zeeland, Mich.) at 20° C. and was allowed to stir for 1 h affording a THF solution of the above-titled complex.

Example 70

Na$_2${[AlH$_3$]$_2$[(S)-PEA]}. 1 mL of a 1 M solution of (S)-α-phenylethylamine ("(S)-PEA") (Zeeland Chemicals, Zeeland, Mich.) in THF was added dropwise to 0.112 g of sodium aluminum hydride at 20° C. and was allowed to stir for 1 h affording a THF solution of the above-titled complex.

Example 71

[NaAlH$_2$((S)-PEA)]$_n$. 2 mL of a 1 M solution of (S)-α-phenylethylamine ("(S)-PEA") (Zeeland Chemicals, Zeeland, Mich.) in THF were added dropwise to 0.112 g of sodium aluminum hydride at 20° C. and was allowed to stir for 1 h affording a THF solution of the above-titled complex.

Example 72

(S)-PEA{Na[AlH((S)-PEA)]$_n$}$_2$. 3 mL of a 1 M solution of (S)-α-phenylethylamine ("(S)-PEA") (Zeeland Chemicals, Zeeland, Mich.) in THF were added dropwise to 0.112 g of sodium aluminum hydride at 20° C. The resulting solution was allowed to stir for 1 h affording a THF solution of the above-titled complex.

Example 73

NaAlH$_2$[(S)-PROP]. 4.1 mL of an 0.54 M solution of (S)-PROP obtained from the procedure of Example 9 in THF were added dropwise to 0.112 g of sodium aluminum hydride at 20 ° C. The resulting solution was allowed to stir for 1 h affording a THF solution of the above-titled complex.

Example 74

NaAlH(OEt)[(S)-PROP]. 6.53 mL of a 0.306 M solution of NaAlH$_3$(OEt) in THF was added dropwise to 4 mL of an 0.5 M solution (THF) of (S)-PROP obtained from the procedure of Example 9 at 20° C. The resulting solution was allowed to stir for 1 h affording a THF solution of the above-titled complex.

Example 75

NaAlH$_2$(IXF). A 5 mL solution (THF) of 0.252 g of IXF obtained from the procedure of Example 24 was added dropwise to 0.0716 g of sodium aluminum hydride in 5 mL of THF at 0° C. The resulting solution was allowed to stir at that temperature for 15 min. affording a THF solution of the above-titled complex.

Example 76

NaAlH(IXF)(OMe). A 5 mL solution (THF) of 0.0424 g of MeOH was added dropwise to 0.0716 g of sodium aluminum hydride in 5 mL of THF at 0° C. The resulting solution was allowed to stir at that temperature for 15 min. To the resulting solution was added 0.252 g of IXF obtained from the procedure of Example 24 in 12 mL of THF. The resulting solution was allowed to stir at that temperature for 15 min. affording a THF solution of the above-titled complex.

Example 77

NaAlH$_2$((+)-DDM). A 15 mL solution (THF) of 0.618 g of (+)-DDM (Aldrich Chemical Co., Milwaukee, Wis.) was added dropwise to 0.0716 g of sodium aluminum hydride in 5 mL of THF at 20° C. The resulting solution was allowed to stir at that temperature for 20 min. affording a THF solution of the above-titled complex.

Example 78

NaAlH(BAP). 0.25 mmol of sodium aluminum hydride and 0.25 mmol of BAP obtained from the procedure of Example 25 were mixed in the presence of 5 mL of THF and were allowed to stir at least 10 min. affording a THF solution of the above-titled complex.

Example 79

NaAlH$_2$(DPP). To a 4.85 mL solution (THF) of 1.25 mmol of sodium aluminum hydride was added a 4 mL solution (THF) of 1.02 g of (S)-(-)-α,α-diphenyl-2-pyrrolidinemethanol ("DPP") (Aldrich Chemical Co., Milwaukee, Wis.). The resulting solution was allowed to stir at room temperature for 5 min. affording a THF solution of the above-titled complex.

Example 80

NaAlH(DPP)(OMe). 0.25 mmol of sodium aluminum hydride and 0.25 mmol of (S)-(-)-α,α-diphenyl-2-pyrrolidinemethanol ("DPP") (Aldrich Chemical Co., Milwaukee, Wis.) were mixed in the presence of THF and were allowed to stir at least 10 min. To the resulting solution was added 0.25 mmol of MeOH in THF affording a THF solution of the above-titled complex.

Example 81

NaAlH(DPP)(OEt). 0.25 mmol of sodium aluminum hydride and 0.25 mmol of (S)-(-)-α,α-diphenyl-2-pyrrolidinemethanol ("DPP") (Aldrich Chemical Co., Milwaukee, Wis.) were mixed in the presence of THF and were allowed to stir at least 10 min. To the resulting solution was added 0.25 mmol of EtOH in THF affording a THF solution of the above-titled complex.

Example 82

NaAlH(DPP) (OPh). A 1 mL solution of 1 M phenol in THF was added dropwise to an 0.258M solution of sodium aluminum hydride in 3.88 mL of THF. The reaction mixture was diluted with 11 mL of THF and was allowed to stir at room temperature. To the resulting solution was added an 0.25M solution of (S)-(-)-α,α-diphenyl-2-pyrrolidinemethanol ("DPP") (Aldrich Chemical Co., Milwaukee, Wis.) in 4 mL of THF. The resulting solution was diluted with 11 mL of THF and was agitated for 1 h affording a THF solution of the above-titled complex.

Example 83

NaAlH(IXF)(OPh). A 5 mL solution (THF) of 0.125 g of phenol was added dropwise to 0.0716 g of sodium aluminum hydride in 5 mL of THF at 20° C. The resulting solution was allowed to stir at that temperature for 5 min. To the resulting solution was added 0.252 g of IXF obtained from the procedure of Example 24 in 10 mL of THF. The resulting solution was allowed to stir at that temperature for 10 min. affording a THF solution of the above-titled complex.

Example 84

NaAlH(IXF)(OPh-p-tert-Bu). A 5 mL solution (THF) of 0.199 g of p-tertbutylphenol (p-tert-BuPhOH) was added dropwise to 0.0716 g of sodium aluminum hydride in 5 mL of THF at 20° C. The resulting solution was allowed to stir at that temperature for 5 min. To the resulting solution was added 0.252 g of IXF obtained from the procedure of Example 24 in 10 mL of THF. The resulting solution was allowed to stir at that temperature for 10 min. affording a THF solution of the above-titled complex.

Example 85

NaAlH(OPh)[(S)-PROP]. To 5.85 mL of a 0.258 M solution (THF) of sodium aluminum hydride was added, dropwise, 1.5 mL of a 1M solution (THF) of phenol, followed by 3 mL of an 0.5M solution (THF) of (S)-PROP obtained from the procedure of Example 9 at 20° C. The resulting solution was diluted with 1.5 mL of THF and allowed to stir at room temperature for 10 min. affording a THF solution of the above-titled complex.

Example 86

$NaAlH_2(CXF)$. To a 5 mL solution (THF) of 0.0716 g of sodium aluminum hydride was added a 15 mL solution (THF) of 0.305 g of 1,2-O-cyclohexylidene-α-D-xylofuranose (CXF) obtained according to the procedure of Example 26. The resulting solution was allowed to stir at room temperature for 15 min. affording a THF solution of the above-titled complex.

Example 87

NaAlH(CXF)(OMe). A 5 mL solution (THF) of 1.325 mmol of MeOH was added dropwise to 0.0716 g of sodium aluminum hydride in 5 mL of THF at 20° C. The resulting solution was allowed to stir at that temperature for 5 min. To the resulting solution was added 0.305 g of CXF obtained from the procedure of Example 26 in 10 mL of THF. The resulting solution was allowed to stir at that temperature for 10 min. affording a THF solution of the above-titled complex.

Example 88

NaAlH(CXF)(O-1-Me-CyBu). A 5 mL solution (THF) of 1.325 mmol of 1-methylcyclobutan-1-ol, obtained from the addition of 1 eq. of methyl magnesium bromide to 1 eq. of cyclobutanone, was added dropwise to 0.0716 g of sodium aluminum hydride in 5 mL of THF at 20° C. The resulting solution was allowed to stir at that temperature for 5 min. To the resulting solution was added 0.305 g of CXF obtained from the procedure of Example 26 in 10 mL of THF. The resulting solution was allowed to stir at that temperature for 10 min. affording a THF solution of the above-titled complex.

Example 89

NaAlH(CXF)(OPh). A 5 mL solution (THF) of 1.325 mmol of phenol was added dropwise to 0.0716 g of sodium aluminum hydride in 5 mL of THF at 20° C. The resulting solution was allowed to stir at that temperature for 5 min. To the resulting solution was added 0.305 g of CXF obtained from the procedure of Example 26 in 10 mL of THF. The resulting solution was allowed to stir at that temperature for 10 min. affording a THF solution of the above-titled complex.

Example 90

NaAlH(CXF)(OPh-p-tert-Bu). A-5 mL solution (THF) of 1.325mmol of p-tertbutylphenol (p-tert-BuPhOH) was added dropwise to 0.0716 g of sodium aluminum hydride in 5 mL of THF at 20° C. The resulting solution was allowed to stir at that temperature for 5 min. To the resulting solution was added 0.305 g of CXF obtained from the procedure of Example 26 in 10 mL of THF. The resulting solution was allowed to stir at that temperature for 10 min. affording a THF solution of the above-titled complex.

Example 91

NaAlH(CXF)(2-NfOH). A 5 mL solution (THF) of 1.325mmol of 2-naphthol (2-NfOH) was added dropwise to 0.0716 g of sodium aluminum hydride in 5 mL of THF at 20° C. The resulting solution was allowed to stir at that temperature for 5 min. To the resulting solution was added 0.305 g of CXF obtained from the procedure of Example 26 in 10 mL of THF. The resulting solution was allowed to stir at that temperature for 10 min. affording a THF solution of the above-titled complex.

Example 92

NaAlH(S-PA). A 15 mL solution (THF) of 0.20 g of S-phenylalininol (S-PA) obtained according to the procedure of Example 27 was added dropwise to 0.0716 g of sodium aluminum hydride in 5 mL of THF at 20° C. The resulting solution was allowed to stir at that temperature for 15 min. affording a THF solution of the above-titled complex.

Example 93

$NaAlH_3$(S-DMPA). A 1 mL solution (THF) of 1M (S)-DMPA obtained according to the procedure of Example 28 was added dropwise to 3.88 mL of an 0.258M solution (THF) of sodium aluminum hydride at room temperature. The resulting solution was allowed to stir at that temperature for 10 min. affording a THF solution of the above-titled complex.

Example 94

$NaAlH_2(S-DMPA)_2$. An 0.5 mL solution (THF) of 1M (S)-DMPA obtained according to the procedure of Example 28 was added dropwise to 2.44 mL of a THF solution of $NaAlH_3$(S-DMPA) obtained according to the procedure of Example 84 at room temperature. The resulting solution was allowed to stir at that temperature for 10 min. affording a THF solution of the above-titled complex.

Example 95

$NaAlH[_2(+)-PDOL]$. To a 7 mL solution (THF) of 0.2 g of (1S,2S,3R,5R)-(+)-pinanediol ("(+)-PDOL") (Aldrich Chemical Co., Milwaukee, Wis.) was added dropwise a 5 mL solution (THF) of 0.0716 g of sodium aluminum hydride at 20° C. The resulting solution was allowed to stir at that temperature for 20 min. affording a THF solution of the above-titled complex.

Example 96

NaAlH[(+)-PDOL](OMe). A solution of 0.64 mmol of MeOH and a solution of 0.64 mmol of (+)-PDOL (total 5 mL of THF) were consecutively added dropwise to a solution (THF) of 0.64 mmol of sodium aluminum hydride at 20° C. The resulting solution was allowed to stir at that temperature for 10 min. affording a THF solution of the above-titled complex.

Example 97

NaAlH[(+)-PDOL][N-Me-(S)-PEA]. A solution (THF) of 0.32 mmol of sodium aluminum hydride was added dropwise to 0.32 mmol of N-methyl-(S)-α-phenylethylamine (N-Me-(S)-PEA) (Zeeland Chemicals, Zeeland, Mich.). The resulting solution was allowed to stir for 10 min. To the resulting solution was added a 2 mL solution (THF) of 0.32 mmol of (+)-PDOL. The resulting solution was allowed to stir for 20 min. affording a THF solution of the above-titled complex.

Example 98

NaAlH[(+)-PDOL][(S)-1-OBu-2-Me]. An 0.5 mL solution (THF) of 0.32 mmol of (S)-(−)-2-methyl-1-butanol (Fluka Chemical Co., Ronkonkoma, N.Y.) [(S)-1-OBu-2-Me] was added dropwise to a 1 mL solution (THF) of 0.32 mmol of sodium aluminum hydride over 10 min. To the resulting solution was added a 1 mL solution (THF) of 0.32 mmol of (+)-PDOL. The resulting solution was allowed to stir for 30 min. affording a THF solution of the above-titled complex.

Example 99

NaAlH[(+)-PDOL](OPh). An 0.5 mL solution (THF) of 0.32 mmol of phenol was added dropwise to a 1 mL solution (THF) of 0.32 mmol of sodium aluminum hydride over 10 min. To the resulting solution was added a 1 mL solution (THF) of 0.32 mmol of (+)-PDOL. The resulting solution was allowed to stir for 30 min. affording a THF solution of the above-titled complex.

Example 100

$NaAlH_2(BDG)_2$. A 1 mL solution (THF) of 0.64 mmol of BDG obtained from the procedure of Example 13 was added dropwise to a 1 mL solution (THF) of 0.32 mmol of sodium aluminum hydride at 20° C. The resulting solution was allowed to stir for 30 min. affording a THF solution of the above-titled complex.

Example 101

$NaAlH(BDG)_3$. A 1.8 mL solution (THF) of 0.96 mmol of BDG obtained from the procedure of Example 13 was added dropwise to a 1 mL solution (THF) of 0.32 mmol of sodium aluminum hydride at 20° C. The resulting solution was allowed to stir for 30 min. affording a THF solution of the above-titled complex.

Example 102

NaAlH(CXF)(1-NfOH). A 5 mL solution (THF) of 1.325mmol of 1-naphthol (1-NfOH) was added dropwise to 0.0716 g of sodium aluminum hydride in 5 mL of THF at 20° C. The resulting solution was allowed to stir at that temperature for 5 min. To the resulting solution was added 0.305 g of CXF obtained from the procedure of Example 26 in 10 mL of THF. The resulting solution was allowed to stir at that temperature for 10 min. affording a THF solution of the above-titled complex.

Example 103

NaAlH((+)-DDM)(OMe). An 8 mL solution (THF) of 0.0185 g of methanol and 0.27 g of (+)-DDM was added dropwise to 0.0312 g of sodium aluminum hydride in 2.2 mL of THF at room temperature under argon. The resulting solution was allowed to stir at room temperature for 5 min. affording a THF solution of the above-titled complex.

Example 104

NaAlH((+)-DDM)(OEt). A 3 mL solution (THF) of 0.663 mmol of ethanol was added dropwise to 0.0358 g of sodium aluminum hydride in 2.5 mL of THF at room temperature. To the resulting solution was added a 5 mL solution (THF) of 0.310 g of (+)-DDM. The resulting solution was allowed to stir at room temperature for 5 min. affording a THF solution of the above-titled complex.

Example 105

NaAlH((+)-DDM)(O-tertBu). A 3 mL solution (THF) of 0.663 mmol of tert-butanol was added dropwise to 0.0358 g of sodium aluminum hydride in 2.5 mL of THF at room temperature. To the resulting solution was added a 5 mL solution (THF) of 0.310 g of (+)-DDM. The resulting solution was allowed to stir at room temperature for 5 min. affording a THF solution of the above-titled complex.

Example 106

NaAlH((+)-DDM)(OPh). A 3 mL solution (THF) of 0.663 mmol of phenol was added dropwise to 0.0358 g of sodium aluminum hydride in 2.5 mL of THF at room temperature. To the resulting solution was added a 5 mL solution (THF) of 0.310 g of (+)-DDM. The resulting solution was allowed to stir at room temperature for 5 min. affording a THF solution of the above-titled complex.

Example 107

NaAlH((+)-DDM)(1-NfOH). A 3 mL solution (THF) of 0.663 mmol of 1-naphthol (1-NfOH) was added dropwise to 0.0358 g of sodium aluminum hydride in 2.5 mL of THF at room temperature. To the resulting solution was added a 5 mL solution (THF) of 0.310 g of (+)-DDM. The resulting solution was allowed to stir at room temperature for 5 min. affording a THF solution of the above-titled complex.

Example 108

$NaAlH[(S)-DMPA]_3$. A 1 mL solution (THF) of 0.75 mmol of (S)-DMPA obtained according to the procedure of Example 28 was added dropwise to a 1.4–2 mL solution (THF) of 0.25 mmol of sodium aluminum hydride at room temperature. The resulting solution was allowed to stir at room temperature for 5 min. affording a THF solution of the above-titled complex.

Example 109

$NaAlH_2[(S)-DMPA](OMe)$. A 1 mL solution (THF) of 0.25 mmol of (S)-DMPA obtained according to the procedure of Example 28 was added dropwise to a 1.4–2 mL solution (THF) of 0.25 mmol of sodium aluminum hydride at room temperature. To the resulting solution was added 0.25 mL of a 1M solution (THF) of methanol. The resulting solution was allowed to stir at room temperature for 5 min. affording a THF solution of the above-titled complex.

Example 110

$NaAlH[(S)-DMPA](OMe)_2$. A 1 mL solution (THF) of 0.25 mmol of (S)-DMPA obtained according to the procedure of Example 28 was added dropwise to a 1.4–2 mL solution (THF) of 0.25 mmol of sodium aluminum hydride at room temperature. To the resulting solution was added 0.5 mL of a 1M solution (THF) of methanol. The resulting solution was allowed to stir at room temperature for 5 min. affording a THF solution of the above-titled complex.

Example 111

$NaAlH[(S)-DMPA]_2(OMe)$. A 1 mL solution (THF) of 0.5 mmol of (S)-DMPA obtained according to the procedure of Example 28 was added dropwise to a 1.4–2 mL solution (THF) of 0.25 mmol of sodium aluminum hydride at room temperature. To the resulting solution was added 0.25 mL of a 1M solution (THF) of methanol. The resulting solution was allowed to stir at room temperature for 5 min. affording a THF solution of the above-titled complex.

Example 112

NaAlH2[(S)-DMPA](O-tertBu). A 1 mL solution (THF) of 0.25 mmol of (S)-DMPA obtained according to the procedure of Example 28 was added dropwise to a 1.4–2 mL solution (THF) of 0.25 mmol of sodium aluminum hydride at room temperature. To the resulting solution was added 0.25 mL of a 1M solution (THF) of tert-butanol. The resulting solution was allowed to stir at room temperature for 5 min. affording a THF solution of the above-titled complex.

Example 113

NaAlH[(S)-DMPA](O-tertBu)$_2$. A 1 mL solution (THF) of 0.25 mmol of (S)-DMPA obtained according to the procedure of Example 28 was added dropwise to a 1.4–2 mL solution (THF) of 0.25 mmol of sodium aluminum hydride at room temperature. To the resulting solution was added 0.5 mL of a 1M solution (THF) of tert-butanol. The resulting solution was allowed to stir at room temperature for 5 min. affording a THF solution of the above-titled complex.

Example 114

NaAlH[(S)-DMPA]$_2$(0-tertBu). A 1 mL solution (THF) of 0.5 mmol of (S)-DMPA obtained according to the procedure of Example 28 was added dropwise to a 1.4–2 mL solution (THF) of 0.25 mmol of sodium aluminum hydride at room temperature. To the resulting solution was added 0.25 mL of a 1M solution (THF) of tert-butanol. The resulting solution was allowed to stir at room temperature for 5 min. affording a THF solution of the above-titled complex.

Example 115

NaAlH[(S)-DMPA]$_2$(OAr). A 1 mL solution (THF) of 0.25 mmol of (S)-DMPA obtained according to the procedure of Example 28 was added dropwise to a 1.4–2 mL solution (THF) of 0.25 mmol of sodium aluminum hydride at room temperature. To the resulting solution was added 0.5 mL of a 1M solution (THF) of 8-hydroxyquinoline (HOAr). The resulting solution was allowed to stir at room temperature for 5 min. affording a THF solution of the above-titled complex.

Example 116

NaAlH$_2$[(S,S)-BDHP]. A 15 mL solution (THF) of 0.293 g of (3S,4S)-1-benzyl-3,4-dihydroxypyrrolidine ((S,S)-BDHP) obtained according to the procedure of Example 29 was added dropwise to a 5 mL solution (THF) of 0.0716 g of sodium aluminum hydride at 20° C. The resulting solution was allowed to stir at room temperature for 30 min. affording a THF solution of the above-titled complex.

Example 117

NaAlH[(S,S)-BDHP](OMe). A 15 mL solution (THF) of 0.043 g of methanol was added to a 5 mL solution (THF) of 0.0716 g of sodium aluminum hydride at room temperature. The resulting solution was allowed to stir at room temperature for 15 min. To the resulting solution was added dropwise 0.256 g of (3S,4S)-1-benzyl-3,4-dihydroxypyrrolidine ((S,S)-BDHP) obtained according to the procedure of Example 29. The resulting solution was allowed to stir at room temperature affording a THF solution of the above-titled complex.

Example 118

NaAlH(BDG)$_2$(OMe). 0.01 mL of methanol followed by a 1.8 mL solution (THF) of 0.21 g of BDG obtained from the procedure of Example 13 were added dropwise to a 1 mL solution (THF) of 0.32 mmol of sodium aluminum hydride at 20° C. The resulting solution was allowed to stir for 10 min. and was then heated at 40° C. for 10 min. affording a THF solution of the above-titled complex.

Example 119

NaAlH$_2$(TDG)$_2$. A 1.8 mL solution (THF) of 0.3 g of 1-O-triphenylmethyl-3,5:4,6-di-O-ethylidene-D-glucitol (TDG) obtained according to the procedure of Example 30 was added dropwise to a 1 mL solution (THF) of 0.032 mmol of sodium aluminum hydride at 20° C. The resulting solution was allowed to stir for 20 min. affording a THF solution of the above-titled complex.

Example 120

NaAlH(TDG)$_3$. A 1.8 mL solution (THF) of 0.45 g of 1-O-triphenylmethyl-3,5:4,6-di-O-ethylidene-D-glucitol (TDG) obtained according to the procedure of Example 30 was added dropwise to a 1 mL solution (THF) of 0.032 mmol of sodium aluminum hydride at 20° C. The resulting solution was allowed to stir for 10 min. and was then heated at 40° C. for 10 min. affording a THF solution of the above-titled complex.

Example 121

Na$_2$Al2H$_2$[(S)-BINOL]$_3$. A mixture of 1.57 g of sodium aluminum hydride and a 5 mL solution (THF) of 0.873 g of (S)-binol obtained from Example 8 was added, and the resulting mixture was allowed to stir at 21° C. for 15 min affording a THF solution of the above-titled complex.

Example 122

NaAlH(TDG)$_3$. A 1.8 mL solution (THF) of 0.45 g of 1-O-triphenylmethyl-3,5:4,6-di-O-ethylidene-D-glucitol (TDG) obtained according to the procedure of Example 30 was added dropwise to a 1 mL solution (THF) of 0.032 mmol of sodium aluminum hydride at 20° C. The resulting solution was allowed to stir for 10 min. and was then heated at 40° C. for 10 min. affording a THF solution of the above-titled complex.

Example 123

NaAlH$_2$(AMP). A solution (THF) of 1 eq. of (S)-2-(anilinomethyl)pyrrolidine ("AMP") (Aldrich Chemical Co. Milwaukee, Wis.) was added dropwise to a solution (THF) of 1 eq. of sodium aluminum hydride. The resulting solution was allowed to stir at room temperature for 60 min. affording an 0.25M solution (THF) of the above-titled complex.

Example 124

NaAlH(AMP)(OMe). A solution (THF) of 1 eq. of AMP followed by a solution (THF) of 1 eq. of methanol was added dropwise to a solution (THF) of 1 eq. of sodium aluminum hydride. The resulting solution was allowed to stir at room temperature for 60 min. affording an 0.25M solution (THF) of the above-titled complex.

Example 125

NaAlH(AMP)(OPh). A solution (THF) of 1 eq. of AMP followed by a solution (THF) of 1 eq. of phenol was added dropwise at −70° C. to a solution (THF) of 1 eq. of sodium aluminum hydride. The resulting solution was allowed to stir at room temperature for 60 min. affording a 1 M solution (THF) of the above-titled complex.

Example 126

NaAlH (AMP) (NPh$_2$). A solution (THF) of 1 eq. of AMP followed by a solution (THF) of 1 eq. of diphenylamine was added dropwise at −70° C. to a solution (THF) of 1 eq. of sodium aluminum hydride. The resulting solution was allowed to stir at room temperature for 60 min. affording a 1M solution (THF) of the above-titled complex.

Example 127

NaAlH$_2$((+)-DDM). A solution (diglyme) of 0.6 mmol of ((+)-DDM) was added dropwise to a solution (diglyme) of 0.6 mmol of sodium aluminum hydride at 20° C. The resulting solution was allowed to stir at room temperature for 5 min. affording an 0.07M (diglyme) solution of the above-titled complex.

Example 128

NaAlH((+)-DDM)(OEt-2-OMe). A solution (diglyme) of 0.6 mmol of (+)-DDM followed by a solution (diglyme) of 0.6 mmol of 2-methoxyethanol was added dropwise to a solution (diglyme) of 0.6 mmol of sodium aluminum hydride at 20° C. The resulting solution was allowed to stir at room temperature for 5 min. affording an 0.07M (diglyme) solution of the above-titled complex.

Example 129

NaAlH((+)-DDM)(OEt-2-OMe). A solution (3:1 diglyme:THF) of 0.6 mmol of (+)-DDM followed by a solution (3:1 diglyme:THF) of 0.6 mmol of 2-methoxyethanol was added dropwise to a solution (3:1 diglyme:THF) of 0.6 mmol of sodium aluminum hydride at 20° C. The resulting solution was allowed to stir at room temperature for 5 min. affording an 0.07M solution (3:1 diglyme:THF) of the above-titled complex.

Example 130

NaAlH$_2$(DTM2). A solution (THF) of 1 eq. of (S)-(−)-α,α-diphenyl-(1,2,3,4-tetrahydroisoquinolin-3-yl)-methanol ("DTM2") obtained according to the procedure of Example 41 was added dropwise to a solution (THF) of 1 eq. of sodium aluminum hydride at 25° C. The resulting solution was allowed to stir at room temperature for 45 min. affording a THF solution of the above-titled complex.

Example 131

Na$_2$Al$_7$H$_2$(DTM2)$_3$. A solution (THF) of 1.5 eq. of (S)-α,α-diphenyl-(1,2,3,4-tetrahydroisoquinolin-3-yl)-methanol ("DTM2") obtained according to the procedure of Example 41 was added dropwise to a solution (THF) of 1 eq. of sodium aluminum hydride at 20° C. The resulting solution was allowed to stir at room temperature for 20 min. affording a THF solution of the above-titled complex.

Example 132

NaAlH$_2$(β-DND). A solution (THF) of 0.3 mmol of (4R,5R)-2,2-dimethyl-α,α,α',α',-tetra-(2-naphthyl)-dioxolane-4,5-dimethanol ("β-DND") (Aldrich Chemical Co., Milwaukee, Wis.) was added dropwise to a solution (THF) of 0.3 mmol of sodium aluminum hydride at 25° C. The resulting solution was allowed to stir at room temperature for 60 min. affording a THF solution of the above-titled complex.

Example 133

NaAlH$_2$(β-DND). A solution (diglyme) of 0.2 mmol of β-DND was added dropwise to a solution (diglyme) of 0.2 mmol of sodium aluminum hydride at 17° C. The resulting solution was allowed to stir at room temperature for 60 min. affording a diglyme solution of the above-titled complex.

Example 134

Na$_2$Al$_2$H$_2$(β-DND)$_3$. A solution (THF) of β-DND was added dropwise to a solution.(THF) of 0.6 mmol of sodium aluminum hydride at 17° C. The resulting solution was allowed to stir at room temperature for 7 min. affording a THF solution of the above-titled complex.

Example 135

NaAlH$_2$(CXF). A solution (diglyme) of 0.6 mmol of CXF obtained according to the procedure of Example 26 was added dropwise to a solution (THF) of 0.6 mmol of sodium aluminum hydride at 17° C. The resulting solution was allowed to stir at room temperature for 10 min. affording a THF solution of the above-titled complex.

Example 136

NaAlH$_2$(CYTOL). A solution (diglyme) of 2.6 mmol of CYTOL obtained according to the procedure of Example 33 was added dropwise to an 0.3–0.4M solution (diglyme) of 2.6 mmol of sodium aluminum hydride at 17° C. The resulting solution was allowed to stir at room temperature for 25 min. affording a THF solution of the above-titled complex.

CHIRAL HYDRIDE COMPLEXES COMPRISING A SOLID PHASE SUPPORT

Example 137

2,3-O-(Cyclohexylidene-4-carboxylic acid)-1,1,4,4-tetraphenyl-L-threitol. Ethyl 4-oxocyclohexanecarboxylate (Aldrich Chemical Co., Milwaukee, Wis.) is reduced with excess lithium aluminum hydride in tetrahydrofuran to provide 4-(hydroxymethyl)cylohexan-1-ol.

The 4-(hydroxymethyl)cylohexan-1-ol obtained above is treated with 1 eq. of acetic anhydride and 2 eq. of pyridine to provide 4-acetoxymethylcylohexan-1-ol.

The 4-(acetoxymethyl)cylohexan-1-ol obtained above is oxidized with 3.0 equivalents of pyridinium dichromate in refluxing methylene chloride to afford 4-(acetoxymethyl)cyclohexan-1-one.

A mixture of 4-(acetoxymethyl)cyclohexan-1-one obtained above, dimethyl L-tartrate and p-TsOH are heated together according to the method described in Example 33 to afford dimethyl-2,3-O-(4-acetoxy)methylcyclohexylidene-L-tartrate.

The dimethyl-2,3-O-(4-acetoxy)methylcyclohexylidene-L-tartrate obtained above is diluted in methanol and treated with excess potassium carbonate to afford, following filtration of the excess potassium carbonate and concentration of the filtrate, dimethyl-2,3-O-(4-hydroxy)methylcyclohexylidene-L-tartrate.

The dimethyl-2,3-O-(4-hydroxy)methylcyclohexylidene-L-tartrate obtained above is treated with 5.5 eq. of phenyl magnesium bromide according to the procedure of Example 33 to obtain 2,3-O -(4-hydroxy)methylcyclohexylidene-1,1,4,4-tetra-phenyl-L-threitol.

The 2,3-O-(4-hydroxy)methylcyclohexylidene-1,1,4,4-tetra-phenyl-L-threitol obtained above is oxidized with 3.0 equivalents of pyridinium dichromate in refluxing methylene chloride to afford the above-titled compound.

Example 138

2,3-O-(Cyclohexylidene-4-carboxylic acid)-1,1,4,4-tetra-phenyl-L-threitol-Grafted Polyacrylamide. A mixture of polyacrylamide and 2,3-O-(cyclohexylidene-4-carboxylic acid)-1,1,4,4-tetra-phenyl-L-threitol (0.02 eq. per acrylamide unit) obtained by the procedure of Example 137 in toluene is allowed to heat at reflux for 24 h, affording the above-titled polymer.

Example 139

$NaAlH_2$(2,3-O-(Cyclohexylidene-4-carboxylic acid)-1,1,4,4-tetra-phenyl-L-threitol-Grafted Polyacrylamide). A solution (diglyme) of 2.6 mmol of cyclohexylidene-4-carboxylic acid)-1,1,4,4-tetra-phenyl-L-threitol-grafted polyacrylamide obtained according to the procedure of Example 138 is added dropwise to an 0.3–0.4M solution (diglyme) of 2.6 mmol of sodium aluminum hydride at 17° C. The resulting solution is allowed to stir at room temperature for 25 min. affording a THF solution of the above-titled complex.

The above-titled complex is useful for enantioselectively reducing a chemical entity having a carbonyl group or carbonyl equivalent.

Example 140

A mixture of 0.3 eq. of β-cyclodextrin and 1 eq. of $NaAlH_4$ is allowed to stir in THF at room temperature for 24 h to afford a chiral hydride complex capable of enantioselectively reducing a chemical entity having a carbonyl group or carbonyl equivalent.

Example 141

1 Equivalent of polyvinyl alcohol (per vinyl alcohol repeat unit), 1 equivalent of $NaAlH_4$ and 1 eq. of (+)-DDM are combined in THF at room temperature and allowed to stir at room temperature for 24 h to afford a chiral hydride complex capable of enantioselectively reducing a chemical entity having a carbonyl group or carbonyl equivalent.

Example 142

1 Equivalent of polyacrylic acid (per acrylic acid repeat unit), 5 equivalents of thionyl chloride and catalytic dimethyl formamide are heated at reflux for 5 h. Concentration of the unreacted thionyl chloride affords polyacryloyl chloride.

Example 143

A mixture of 1 equivalent of polyacryloyl chloride (per acryloyl chloride repeat unit) obtained according to the procedure of Example 142 and 0.1 equivalent of S-(+)-2-amino-1-butanol (Aldrich Chemical Co., Milwaukee, Wis.) is allowed to stir in methylene chloride for 5 h to afford a methylene chloride solution of S-(+)-2-amino-1-butanol-functionalized polyacryloyl chloride.

The methylene chloride solution of S-(+)-2-amino-1-butanol-functionalized polyacryloyl chloride is concentrated, and diluted with THF. To the THF solution is added, at 0° C., excess water and catalytic HCl. The resulting mixture is allowed to warm to room temperature and stir at that temperature for 24 h to afford an aqueous THF solution of S-(+)-2-amino-1-butanol-functionalized polyacrylic acid.

The aqueous THF solution of S-(+)-2-amino-1-butanol-functionalized polyacrylic acid is treated with 0.9 equivalents of sodium bicarbonate, to afford an aqueous solution of sodium S-(+)-2-amino-1-butanol-functionalized polyacrylate.

The aqueous solution of sodium S-(+)-2-amino-1-butanol-functionalized polyacrylate is concentrated in vacuo to remove the THF, then lyophilized to afford solid sodium S-(+)-2-amino-1-butanol-functionalized polyacrylate.

To THF is added, at room temperature, 0.1 equivalent of 0.1 solid sodium S-(+)-2-amino-1-butanol-functionalized polyacrylate, 0.1 equivalent of $NaAlH_4$ and 0.1 equivalent of MeOH. The resulting mixture is allowed to stir at room temperature for 24 h to afford a chiral hydride complex capable of enantioselectively reducing a chemical entity having a carbonyl group or carbonyl equivalent.

INFRARED SPECTRAL DATA FOR ILLUSTRATIVE CHIRAL HYDRIDE COMPLEXES SYNTHESIZED

Materials and Methods

Solutions of illustrative chiral hydride complexes were obtained according to the procedures of the above Examples. The hydride complexes were stored at room temperature in hermetically capped flasks an aliquots (approx. 1 mL) were removed via syringe for infrared (IR) spectral data. IR spectra were recorded on a Perkin Elmer 577 Spectrometer using a KBr cell (0.218 mm) in THF solvent. Prior to recording the IR spectra, the KBr cell was evacuated and filled with Ar three times. The KBr cell was then washed with THF and the IR spectrum run immediately thereafter. IR data for illustrative hydride complexes of the present invention are shown below in Table 1.

TABLE 1

| Complex | mol/L (THF) | $v_{Al-H}$ (cm$^{-1}$) | optical density (D) | Absorption coefficient ($\epsilon_{max}$) |
| --- | --- | --- | --- | --- |
| $NaAlH_4$ | 0.265 | 1675 | 1 | 275 |
| $NaAlH_3$(OEt) | 0.088 | 1680 | 0.37 | 190 |
| $NaAlH_2$(OEt)$_2$ | 0.088 | 1680, 1760 | 0.25, 0.2 | 125, 100 |
| $NaAlH_2$(DPP) | 0.25 | 1675 | 0.45 | 85 |
| $NaAlH_2$(DBM) | 0.14 | 1680, 1800 | 0.23 | 75 |
| $NaAlH_2$(CXF) | 0.066 | 1660 | 0.2 | 140 |
| $NaAlH$(OEt)$_3$ | 0.088 | 1765 | 0.16 | 80 |
| $NaAlH$(CXF)(OMe) | 0.066 | 1760 | 0.03 | 20 |

TABLE 1-continued

| Complex | mol/L (THF) | $\nu_{Al-H}$ (cm$^{-1}$) | optical density (D) | Absorption coefficient ($\epsilon_{max}$) |
|---|---|---|---|---|
| NaAlH(S)-BINOL](OMe) | 0.155 | 1760 | 0.065 | 20 |
| NaAlH((+)-DDM)(OMe) | 0.057 | 1770 | 0.085 | 70 |
| NaAlH(β-DND)(OMe) | 0.057 | 1770 | 0.07 | 80 |
| NaAlH(BDG)(OMe) | 0.15 | 1780–1900 (broad) | very weak | — |

NMR DATA FOR ILLUSTRATIVE HYDRIDE COMPLEXES

Materials and Methods

NMR experiments were recorded using a Bruker AC-200 NMR spectrometer in THF-$_8$ solvent. THF-d8 was refluxed with sodium aluminum hydride prior to use. An 0.532M solution of sodium aluminum hydride in THF-d$_8$ was used for the preparation of all hydride complexes used in this study. NMR data for illustrative hydride complexes, including NaAlH[(S)-BINOL](OMe), are shown below in Table 2.

TABLE 2

| Sodium Aluminum Complex | $^1$H NMR (δ, ppm) | $^{13}$C NMR (δ, ppm) |
|---|---|---|
| NaAlH$_4$ | 2.8 sext., broad (0–5.5) (J=173 Hz) | — |
| NaAlH$_3$(OMe) | 2.84 sext., broad (0–5.5) (J=173 Hz) ; 3.51 (s, OMe) | 51.76 |
| NaAlH$_2$(OMe)$_2$ | 3.54 (s, OMe) | 51.66 |
| NaAlH(OMe)$_3$ | 3.55 (s, OMe) | 51.65 |
| NaAl(OMe)$_4$/MeOH | 3.61 (s, OMe) 3.40 (s, OMe) 4.91 (s, OH) | 52.06 51.18 |
| NaAlH[(S)-BINOL](OMe) | 3.55 (s, OMe) 3.0–4.2 broad | — |

EXAMPLE: ENANTIOSELECTIVE REDUCTIONS USING ILLUSTRATIVE CHIRAL HYDRIDE COMPLEXES

Example 144

The CXF ligand was prepared in two stages from D-xylose according to the procedure described in Example 26 and in J. Org. Chem, 1965, 30 (4), 1288.

A solution of 1,2-O-cyclohexylidene-α-D-xylofuranose (CXF, 0.305 g, 1.325 mmol) in THF (15 mL) was added with stirring under Ar to solution of sodium aluminum hydride (0.0716 g, 1.325 mmol) in THF (5 mL) for 15 min (r.t.). The mixture was cooled to −70° C. followed by acetophenone injection by a syringe (0.05 mL, 0.44 mmol). The colorless, clear solution was allowed to stand at −70° C. for 20 h and the reaction mixture was hydrolyzed using 90% MeOH until evolution of H$_2$ discontinued (6 mL). The solvent was evaporated in vacuo and resulting residue was extracted by hexane (3×30 mL). The extract was washed with water (3×10 mL) up to pH-7, the solvent evaporated and residue analyzed by GC. Conversion of AP into PET 75%, e.e. 52% (S).

Example 145

A solution of (S)-(−)-α,-α-diphenyl-2-pyrrolidinemethanol (DPP) (Aldrich) (1.02 g, 4.03 mmol) in carefully dried THF (4 mL) was added to a solution of sodium aluminum hydride in THF (4.85 mL of 0.252M solution, 1.25 mmol) with stirring under argon at r.t. for 5 min, 45.5 cm$^3$ H$_2$ being evolved (calcld. 56 mL for AlH$_2$ complex formation). 1.2 mL of the solution thus obtained was placed by syringe in another flask, and was allowed to stand at r.t. for 1 h. The solution was cooled to +70° C. and acetophenone (0.6 mL of 0.133M solution in THF, 0.083 mmol) was added. Within 24 h (−70° C.) the first probe of reaction mixture was taken and analyzed by GC (30 m capillary column, stationary phase was pentylated and trifluoroacetylated γ-cyclodextrine). GC analysis gave 86% conversion of AP into 1-phenylethanol, e.e. 69% (R). After an additional 24 h, the reaction mixture was warmed to −20° C. and was allowed to stand at this temperature for 4 days. GC analysis of the reaction mixture gave conversion of AP 88% and e.e. value 70% (R). After an additional 3 days, the reaction mixture was hydrolyzed using MeOH-ether (1:10) until evolution of H$_2$ ceased. The mixture was diluted by 4-fold volume of ether and extracted by 10% HCl to remove the aluminum compounds and the ligand. The ether layer was separated and analyzed by GC: conversion of AP 91%., e.e. 67% (R).

Example 146

A solution of (+)-DDM (0.27 g, 0.578 mmol) (Aldrich Chemical Co., Milwaukee, Wis.) and MeOH (0.0185 g, 0.578 mmol) in THF (8 mL) was added with stirring at r.t. over 5 min. to solution of sodium aluminum hydride (0.0312 g, 0.578 mmol) in THF (2.2 mL) under Ar. The resulting solution was allowed to stir at room temperature for 1 h. The flask was cooled to 0° C., acetophenone (0.022 mL, 0.193 mmol) was added by syringe and the reaction mixture (clear, colorless solution) was allowed to stand in a refrigerator at 0° C. for 24 h. The mixture was then analyzed by GC. Conversion of AP 8%, e.e. 67 (R). Another probe of the reaction mixture was analyzed by HPLC using chiral stationary phase of Pyrcle type. The second probe gave the same results within ±5% range.

Example 147

The ligand DBM was prepared as disclosed in Example 14 and in J. Chem Soc., Perkin Tran. I., 1997 (10), p. 1123, except that the second recrystallization of the product from methanol was omitted.

D-Mannitol (12.5 g, 70 mmol; Fluka Chemical Corporation, Ronkonkoma, N.Y., CH-9470) and benzaldehyde (Russia, TU-6-09-1672-77; 12.5 g, 140 mmol) were dissolved in pure N,N-dimethylformamide (40 mL, Fluka Chemical Corporation, Ronkonkoma, N.Y.) and treated with conc. H₂SO₄ (Russia, GOST 4204–77; 5 mL) added in one portion. The resulting mixture was allowed to stand for 72 h at r.t. and was then poured into a solution of K₂CO₃ (5 g) in ice-cold water (0.5 L) covered with a layer of hexane. The unreacted aldehyde was extracted into hexane with vigorous stirring, and the aqueous layer was allowed to stand at 5–10° C., depositing a white cheese-like solid thereon. The solid was collected by filtration, air-dried, and recrystallized from CHCl₃. The resulting white crystals were washed with dry hexane (2×10 mL) and benzene (10 mL), then dissolved in hot benzene. The benzene solution was evaporated and the resulting solid residue was dried over P₂O₅ in an Abderhalden apparatus for 18 h at 40° C./0.3 torr. to afford 13.3 g (53%) DBM: mp.=152–153° C. (189–191° C. from MeOH).

A solution of DBM (0.115 g, 0.32 mmol) in THF (1.8 mL) was added dropwise under Ar over 10 min at r.t. to a stirred solution of sodium aluminum hydride (0.32 mmol in 1 mL of THF), and the resulting mixture was warmed to 25° C. for 20 min to attain the full substitution of the two H atoms in sodium aluminum hydride. There evolved 18 cm³ of H₂ (theory: 14.3 mL).

The mixture was then cooled to 0° C. and treated with AP (0.019 mL, 0.16 mmol) in THF (0.4 mL), injected in one portion. The mixture was stirred for 3 h at 0° C., quenched with water (5 mL), and extracted with Et₂O (5 mL). The ether solution was evaporated and the resulting residue was extracted into hexane (2.5 mL) for analysis by GC.

The conversion of AP (GC): 9.5%, e.e. (GC): 95% (S).

Example 148

Abs. methanol (0.01 mL, 0.32 mmol) and carefully washed (hexane) and dried BDG (0.21 g, 0.64 mmol, weight after 12 h at 40° C./10 torr), obtained according to the procedure of Example 13, were dissolved in abs. THF (1.8 mL). The resulting solution was added dropwise over 10 min. at 20° C. (under Ar) to a stirred solution of sodium aluminum hydride (0.32 mmol in 1 mL of THF). The reaction mixture was heated for 10 min. at 40° C. to attain the full substitution of the three H atoms in SAH; the evolution of H₂ was 26.6 cm3 (theory: 21.5 mL). The mixture was then cooled to 20° C. and treated with AP (0.019 mL, 0.16 mmol) in THF (0.4 mL), injected in one portion. Stirring at 20° C. was continued for 3 h, then the reaction was quenched with water (0.5 mL). The reaction mass was filtered prior to analysis through a thin pad of Florisil.

The conversion of AP (GC): 3.5%, e.e. (GC): 93% (R).

ENANTIOMERICALLY ENRICHED ALCOHOLS SYNTHESIZED FROM KETONES AND ILLUSTRATIVE CHIRAL HYDRIDE COMPLEXES

Materials and Methods

Acetophenone ("AP") was used, unless otherwise noted, as an illustrative ketone substrate for reductions using representative chiral hydride complexes of the present invention. Reduction afforded 1-phenylethan-1-ol ("PET") with an excess of either the (R)- or (S)-enantiomer, as indicated. Amounts of individual PET enantiomers were quantified using either the high-performance liquid chromatography (HPLC) or the gas chromatography (GC) method. Hydride reductions were performed in THF, unless otherwise noted.

HPLC Method

Enantiomerically enriched mixtures of PET obtained from the reduction of AP with the chiral hydride complexes of the present invention were converted to their carbamate derivatives using (S)-α-(1-naphthyl)ethylisocyanate and Et₃N so as to provide a more easily separable mixture of (S,R)- and (S,S)-diastereomers.

The above diastereomeric mixtures were separated on a Laboratornj Pristoje Praha HPLC with a HPP 5001 high pressure pump, LCO-2563 UV-VIS detector (λ=254 nm), CI-1002 computing integrator and TZ 4620 line recorder. A 150×3.3 mm column was used with Separon-NH₂ (aminopropylated silica, 5μ) sorbent. The eluent was 0.5:99.5 iPrOH:n-hexane, passed at a rate of 0.6 mL/min. Capacity factors (K') for each component were calculated using the equation K'=(τ−τ₀)/τ₀, where τ is a retention time, τ₀ is that for toluene (1.64 min. under the conditions employed). The retention times (τ) and capacity factor (K') values for diastereomeric adducts were as follows: (S,R): τ=14.4 min., K'=7.78; (S,S): τ=17.5 min., K'=9.65.

GC Method

GC analysis was performed using a Biochrome-J instrument (Russia) with a quartz capillary column (30 m×0.2 mm) containing dipentylated and trifluoroacetylated γ-cyclodextrin (Carbohydrate Res., 131, 209–217 (1984)), film thickness=0.2 mm. $V_{He}$=1 mL/min.; initial column temperature=50° C., raising temperature (8° C./min.2 within 10 min. after probe injection. GC analysis of trifluoroacetylated derivatives of (R)- and (S)-PET (Zh. Analyt. Khim., 1973, 18 (7), 41427) gave completely resolved peaks, with the retention time of the (R)-derivative being longer than that of the (S)-derivative.

Data for illustrative hydride complexes of the present invention, showing ratio of hydride complex:acetophenone (AP), reduction conditions, % yield of 1-phenylethanol (PET) product and enantiomeric excess (e.e.) of either the (R)- or (S)-PET enantiomer are shown below in Table 3:

TABLE 3

| Complex | Ratio (Complex: AP) | Reduction Conditions | % PET | Enantiomeric Excess (e.e.) |
|---|---|---|---|---|
| NaAlH(DIPM)(OMe) | 1:0.33 | −2° C., 120 h | 44% | 33.4% (R), GC |
| NaAlH₂(DES) | 1.1:1 | rt, 10 min | >99% | 15.2% (S), HPLC |
| NaAlH(DES)(OMe) | 1.04:1 | rt, 3 h | 3.3% | 1.5% (S), HPLC |
| NaAlH[(S)—BINOL](OMe) | 1:0.33 | −70 to −18° C., 4 days | 97% | 88% (S), GC |
| NaAlH₂(BCG) | 1:1 | −2° C., 168 h | 84% | 9% (S), GC |
| NaAlH(BCG)(OMe) | 1:1.5 | −20° C., 96 h | 11% | 5.5% (S), GC |
| NaAlH₂(DCG)₂ | 1.1 | −2° C., 96 h | 99% | 3.5% (S), GC |
| NaAlH₂(DCG)₂(OMe) | 1:0.33 | −2° C., 168 h | 16% | 19% (S), GC |
| NaAlH(DCG)₃ | 1:0.33 | −2° C., 144 | 5.5% | 17% (S), GC |
| NaAlH(Eph)(OMe) | 1:0.33 | −2° C., 144 | 15% | 15% (R), GC |
| NaAlH₂(DBM) | 1:0.5 | 0° C., 3 h | 9.5% | 95% (S), GC |

TABLE 3-continued

| Complex | Ratio (Complex: AP) | Reduction Conditions | % PET | Enantiomeric Excess (e.e.) |
|---|---|---|---|---|
| NaAlH[(S)—BINOL](OEt) | 1:0.25 | −70 to −18° C., 4 days | 54% | 84% (S), GC |
| NaAlH(DIPM)(2-NfOH) | 1:0.5 | 0° C., 120 h | 10.5% | 21% (R), GC |
| NaAlH(AG) | 1:1 | 0° C., 48 h | 3% | 7.5% (S), GC |
| NaAlH[(S,S)—BPAP] | 1:0.6 | −18° C., 60 h | 60.5% | 6% (S), GC |
| NaAlH(DBM)(O-isoBu) | 1:0.69 | rt, 24 h | 78.6% | 3.0% (S), GLC |
| NaAlH(DIPM)[(S)—IBPA] | 1:0.7 | 0° C., 96 h | 35% | 25% (R), GC |
| NaAlH(DIPM)[(R)—IBPA] | 1:0.7 | 0° C., 96 h | 31% | 25% (R), GC |
| NaAlH$_2$(BDG)$_2$ | 1:0.7 | 0° C., 3 h | 4.1% | 83.7% (S), GLC |
| NaAlH[(S,S)—BMBE](OMe) | 1:0.33 | −20° C., 24 h | 19% | 5% (R), GC |
| NaAlH$_2$(DIPM) | 1:0.33 | 0° C., 24 h | 68% | 2% (R), GL |
| NaAlH2[(S)—IBPA]$_2$ | 1:0.33 | −20° C., 24 h | 97% | 5% (R), GC |
| NaAlH[(S)—IBPA]$_3$ | 1:0.33 | −20° C., 24 h | 75% | 1.5% (R), GC |
| fNaAlH(OEt)((S)—PEA]$_n$ | 1:0.33 | 0° C., 68 h | 77% | 7.4% (S), GL |
| Na2{[AlH$_2$(OEt)]$_2$[(S)—PEA]} | 1:0.33 | −70° C., 24 h; then −20° C., 22 h | 84% | 9% (S), GC |
| Na$_2${[AlH$_3$]$_2$[(S)—PEA]} | 1:0.33 | 0° C., 72 h | 98% | 2% (S), GC |
| [NaAlH$_2$((S)—PEA)]$_n$ | 1:0.33 | −70° C., 24 h; then −20° C., 72 h | 78% | 4.6% (S), GC |
| (S)—PEA{Na[MH(S)—PEA]$_n$}$_2$ | 1:0.33 | −70° C., 24 h | 48% | 8.4% (S), GC |
| NaAlH2[(S)—PROP] | 1:0.33 | −18° C., 96 h | 15% | 7% (R), GC |
| NaMH[(S)—PROP](OEt) | 1:0.33 | 0° C., 240 h | 20.5% | 3.4% (S), GC |
| NaAlH$_2$(IXF) | 1:0.33 | −75° C., 24 h | 98% | 35% (S), GC |
| NaAlH(IXF)(OMe) | 1:0.33 | 20° C., 3 h | 95% | 25% (S), GC |
| NaAlH(IXF)(OEt) | 1:0.33 | 20° C., 24 h | 99% | 25% (S), GC |
| NaAlH$_2$((+)-DDM) | 1:0.33 | −75° C., 24 h | 96% | 48% (R), GC |
| NaAlH(BAP) | 1:0.33 | 0° C., 66 h | 29% | 5.5% (S), GC |
| NaAlH2(DPP) | 1:0.7 | −70° C., 48 h; then −20° C., 4 days | 91% | 67% (R), GC |
| NaAlH(DPP)(OMe) | 1:0.33 | 0° C., 96 h | 5% | 11% (S), GC |
| NaAlH(DPP)(OEt) | 1:0.33 | −70° C., 24 h; then −20° C., 15 days | 5% | 19% (S), GC |
| NaAlH(DPP)(OPh) | 12:1 | −20° C., 7 days | 60% | 44% (R), GC |
| NaAlH(DPP)(NCy$_2$) | 1:0.33 | −20° C., 7 days | 23% | 9% (S), GC |
| NaAlH(IXF)(OPh) | 1:0.33 | −63° C., 3 h | 97% | 33% (S), GC |
| NaAlH(IXF)(OPh-p-tert-Bu) | 1:0.33 | −75° C., 24 h | 98% | 40% (S), GC |
| NaAlH2[(S)—PROP] | 1:0.33 | −18° C., 96 h | 15% | 7% (S), GC |
| NaAlH[(S)—PROP](OEt) | 1:0.33 | 0° C., 240 h | 20.5% | 3.5% (S), GC |
| NaAlH[(S)—PROP](OPh) | 1:0.33 | −70° C., 24 h; then −20° C., 8 days | 3% | 8% (S), GC |
| NaAlH$_2$(CXF) | 1:0.33 | −75° C., 20 h | 75% | 52% (S), GC |
| NaAlH(CXF)(OMe) | 1:0.33 | −20° C., 3 h | 87% | 28% (S), GC |
| NaAlH(CXF)(O-1-Me—CyBu) | 1:0.33 | 20° C., 18 h | 94% | 26% (S), GC |
| NaAlH(CXF)(OPh) | 1:0.33 | 20° C., 14 h | 74% | 33.5% (S), GC |
| NaAlH(CXF)(OPh-p-tert-Bu) | 1:0.33 | 20° C., 24 h | 96% | 32% (S), GC |
| NaAlH(CFX)(2-NfOH) | 1:0.33 | 20° C., 18 h | 77% | 26.5% (S), GC |
| NaAlH[(S)—PA] | 1:0.33 | −75° C., 48 h | 82% | 4.5% (S), GC |
| NaAlH$_3$((S)—DMPA) | 1:0.33 | 0° C., 24 h | 99% | 4% (S) GC |
| NaAlH$_2$((S)—DMPA)$_2$ | 1:0.33 | −20° C., 24 h | 36% | 19% (R), GC |
| NaAlH$_2$[(+)-PDOL] | 1:0.7 | −10° C., 20 h | 97.5% | 14% (S), GC |
| NaAlH[(+)-PDOL](OMe) | 1:0.5 | 20° C., 20 h | 42.5% | 6% (S), GC |
| NaAlH[(+)-PDOL][N—Me—(S)—PEA] | 1:0.6 | 20° C., 18 h | 67% | 9.5% (S), GC |
| NaAlH[(+)-PDOL][(S)-1-OBu-2-Me] | 1:0.5 | 20° C., 3 h | 1% | 11% (S), GC |
| NaAlH[(+)-PDOL](OPh) | 1:0.5 | 20° C., 3 h | 67% | 8.5% (S), GC |
| NaAlH$_2$(BDG)$_2$ | 1:1 | 0° C., 1.5 h; then 20° C., 22.5 h[1] | 52% | 21.5% (R), GC |
| NaAlH(BDG)$_3$ | 1:1 | −10° C., 70 h | 10% | 89.5% (R), GC |
| NaAlH(CXF)(1-NfOH) | 1:0.33 | −75° C., 48 h | 97% | 46.5% (S), GC |
| NaAlH((+)-DDM)(OMe) | 1:0.33 | 0° C., 24 h | 87% | 67% (R), GC |
| NaAlH((+)-DDM)(OEt) | 1:0.33 | −20° C., 20 h | 93% | 58% (S), GC |
| NaAlH((+)-DDM)(OPh) | 1:0.33 | −20° C., 24 h | 100% | 74% (S), GC |
| NaAlH((+)-DDM)(1-NfOH) | 1:0.33 | −20° C., 24 h | 99.5% | 56% (S), GC |

TABLE 3-continued

| Complex | Ratio (Complex: AP) | Reduction Conditions | % PET | Enantiomeric Excess (e.e.) |
|---|---|---|---|---|
| NaAlH((S)—DMPA)$_3$ | 1:0.33 | 0° C., 68 h | 0.6% | 28% (S), GC |
| NaAlH$_2$((S)—DMPA)(OMe) | 1:0.33 | −70° C., 24 h | 90% | 3% (S), GC |
| NaAlH((S)—DMPA)(OMe)$_2$ | 1:0.33 | −70° C., 24 h | 77% | 2% (S), GC |
| NaAlH((S)—DMPA)2(OMe) | 1:0.33 | 0° C., 44 h | 0.4% | 37% (R), GC |
| NaAlH$_2$((S)—DMPA)(O-tertBu) | 1:0.33 | −20° C., 24 h | 98% | 2.5% (S), GC |
| NaAlH((S)—DMPA)(O-tertBu)$_2$ | 1:0.33 | −70° C., 24 h | 83% | 6.5% (S), GC |
| NaAlH((S)—DMPA)$_2$(O-tertBu) | 1:0.33 | −20° C., 68 h | 11% | 5% (S), GC |
| NaAlH((S)—DMPA)$_2$(OAr) | 1:0.33 | −70° C., 22 h | 0.5% | 26% (S), GC |
| NaAlH$_2$(BDHP) | 1:0.33 | 0° C., 72 h | 97% | 10.5% (S), GC |
| NaAlH(BDHP)(OMe) | 1:0.33 | 0° C., 48 h | 98% | 8.5% (S), GC |
| NaAlH(BDG)$_2$(OMe) | 1:0.5 | 20° C., 3 h | 3.5% | 93% (R), GC |
| NaAlH(BDG)$_3$ | 1:1 | 20° C., 70 h | 7% | 86% (R), GC |
| NaAlH(BDG)$_2$(OEt-2-OMe) | 1:1 | 20 ° C., 70 h | 97% | 2% (R), GC |
| NaAlH$_2$(TDG)$_2$ | 1:0.5 | 20° C., 24 h | 72% | 8% (R), GC |
| NaAlH(TDG)$_3$ | 1:0.5 | 20° C., 70 h | 16% | 1% (S), GC |
| NaAlH$_2$[(S)—BINOL] | 1:0.33 | −70° C., 2 h | 95% | 32% (R), GC |
| NaAlH$_2$[(S)—BINOL] | 1:0.33 | −70° C., 2 h$^2$ | 74% | 42% (S), GC |
| Na$_2$Al$_2$H$_2$[(S)—BINOL]$_3$ | 1:0.33 | −70° C., 2 h | 72% | 73% (S), GC |
| NaAlH$_2$(AMP) | 1:0.33 | −70° C., 3 days | 10% | 15% (R), GC |
| NaAlH(AMP)(OMe) | 1:0.33 | −70° C., 3 days | 14% | 23% (R), GC |
| NaAlH(AMP)(OPh) | 1:0.33 | −70° C., 4 days | 10% | 0.5% (R), GC |
| NAlH(AMP)(NPh$_2$) | 1:0.33 | −70° C., 4 days | 2% | 9.0% (R), GC |
| NaAlH$_2$((+)-DDM) | 1:0.33 | −75° C., 48 h$^2$ | 100% | 91% (R), GC |
| LiAlH$_2$((+)-DDM) | 1:0.33 | 0° C., 27 h$^2$ | 97% | 69% (R), GC |
| NaAlH((+)-DDM)(OEt-2-OMe) | 1:0.33 | 20° C., 24 h$^3$ | 100% | 84% (R), GC |
| NaAlH$_2$(DTM2) | 1:0.34 | 0° C., 96 h | 53% | 70% (R), GC |
| NaAlH$_2$(β-DND) | 1:0.33 | 0° C., 1 day | 99% | 44% (R), GC |
| NaAlH$_2$(β-DND) | 1:0.33 | −20° C., 2 days | 100% | 68% (R), GC |
| Na$_2$Al$_2$H$_2$(CXF)$_3$ | 1:0.33 | −20° C., 1 day | 97% | 13% (S), GC |
| NaAlH$_2$(CXF) | 1:0.33 | −20° C., 1 day$^2$ | 93% | 5% (S), GC |
| NaAlH$_2$(DPP) | 1:0.33 | −70° C., 3 days | 87%$^4$ | 67% (R), GC |
| NaAlH(CXF)(OPh-p-tert-Bu) | 1:0.33 | −20° C., 2 days | 100%$^5$ | 89% (S), HPLC |
| NaAlH$_2$((+)-DDM) | 1:0.33 | −20° C., 2 days$^2$ | 98%$^5$ | 67% (R), HPLC |
| NaAlH$_2$(DPP) | 1:0.33 | −70° C., 5 days; then −20° C., 4 days | 70%$^5$ | 93% (R), HPLC |
| NaAlH$_2$(CYTOL) | 1:0.33 | −20° C., 48 h$^2$ | 84% | 81% (S), GC |
| LiAlH$_2$(CYTOL) | 1:0.33 | 0° C., 19 h$^2$ | 98% | 42% (S), GC |
| NaAlH$_2$(CYTOL) | 1:0.33 | −20° C., 24 h | 98% | 50% (S), GC |
| NaAlH$_2$(CYTOL) | 1:0.33 | −75° C., 24 h$^3$ | 19% | 59% (S), GC |
| NaAlH((+)-DDM) (OEt-2-OMe) | 1:0.33 | 0° C., 18 h$^2$ | 84% | 87% (R), GC |

[1] reaction performed in toluene
[2] reaction performed in diglyme
[3] reaction performed in 3:1 diglyme:THF
[4] ketone substrate was propiophenone; reaction product was 1-phenylpropanol
[5] ketone substrate was 2-acetylfluorene; reaction product was 2-(1-hydroxyethyl)fluorene As can be seen from Table 3, the complexes that are most efficient in terms of yield and e.e., possess a $C_2$ axis of symmetry. Axially disymmetric molecules such as these are thought to be less susceptible to disproportionation reactions and hence provide complexes with a higher degree of enantioselectivity.

It is to be understood that for a particular chiral hydride complex, the chiral ligand thereof will produce an enantiomeric excess of a reduction product such that for that particular hydride complex, the use of the same chiral ligand but of the opposite enantiomer will give rise to the reduction product of the opposite stereochemistry. For example, whereas NaAlH$_2$ ((+)-DDM) reduces acetophenone to (R)-1-phenylethan-1-ol in 91% enantiomeric excess (0° C.; 48 h; diglyme), reduction of acetophenone with NaAlH$_2$ ((−)-DDM) under identical conditions will give an enantiomeric excess of (S)-1-phenylethan-1-ol.

It is to be understood that while most of the illustrative chiral hydride complexes of Table 3 are sodium aluminum hydride complexes, chiral hydride complexes comprising a chiral ligand (R*, R or R*) and optionally an achiral ligand (R' or R") will function effectively to reduce a carbonyl group or a carbonyl equivalent, regardless of whether M is Na$^+$, Li$^+$ or K$^+$, or whether Al is replaced with B.

COMPARISON OF NaAlH[(S)-BINOL](OMe) AND LiAlH[(S)-BINOL](OMe) WITH REGARD TO CONVERSION AND ENANTIOSELECTIVITY

NaAlH[(S)-BINOL](OMe) gave surprisingly and unexpectedly high conversion (chemical yield) and enantioselectivity values relative to LiAlH[(S)-BINOL](OMe), when admixed with acetophenone (AP). In a comparative experiment, NaAlH[(S)-BINOL](OMe) was admixed with AP in THF at −70° C. to afford 79% 1-phenylethanol (PET) with the (S)-enantiomer in 97% enantiomeric excess, whereas under similar conditions, LiAlH((R)-BINOL)(OMe) afforded only 60% PET with the (R)-enantiomer in only 87% enantiomeric excess (J. Am. Chem. Soc., 1984, 106, 6709). Thus, NaAlH[(S)-BINOL](OMe) is surprisingly and unexpectedly a more efficient and enantioselective reducing agent than its lithium analog.

COMPARISON OF NaAlH$_2$(DDM) AND LiAlH$_2$(DDM) WITH REGARD TO CONVERSION AND ENANTIOSELECTIVITY

NaAlH$_2$(DDM) and NaAlH$_2$(CYTOL) gave surprisingly and unexpectedly high conversion and enantioselectivity values relative to their lithium analogs, when admixed with AP. The results are shown below in Table 4:

TABLE 4

| Complex | Reduction Conditions | % PET | Enantiomeric Excess (e.e.) |
|---|---|---|---|
| NaAlH$_2$(DDM) | 0° C.; 20 h | 95% | 74% (R) |
| NaAlH$_2$(DDM) | 22° C.; 25 h | 100% | 84% (R) |
| LiAlH$_2$H(DDM) | 0° C.; 27 h | 100% | 58% (R) |
| LIAlH$_2$H(DDM) | 0° C.; 27 h | 97% | 69% (R) |
| LiAlH$_2$H(DDM) | 20° C.; 27 h | 98% | 66% (R) |
| LiAlH$_2$H(DDM) | 20° C.; 1 h | 97% | 63% (R) |
| NaAlH$_2$(CYTOL) | 0° C.; 24 h | 100% | 65% (S) |
| LiAlH$_2$H(CYTOL) | 0° C.; 19 h | 98% | 42% (S) |
| LiAlH$_2$H(DDM) | 0° C.; 18 h | 100% | 33% (S) |

Thus, NaAlH$_2$(DDM) and NaAlH$_2$(CYTOL) are surprisingly and unexpectedly more efficient and enantioselective reducing agents than their lithium analogs.

The present invention is not to be limited in scope by the specific embodiments disclosed in the examples which are intended as illustrations of a few aspects of the invention and any embodiments which are functionally equivalent are within the scope of this invention. Indeed, various modifications of the invention in addition to those shown and described herein will become apparent to those skilled in the art and are intended to fall within the appended claims.

A number of references have been cited and the entire disclosures of which are incorporated herein by reference.

What is claimed is:

1. A chiral hydride complex of the formula NaAlH$_{2-b}$(R**)(R')$_b$, wherein b is 0–1; and R* is (+)-trans-α,α'-(2,2-Dimethyl-1,3-dioxolane-4,5-diyl)bis(diphenylmethanol) ((+)-DDM) or (−)-trans-α,α'-(2,2-Dimethyl-1,3-dioxolane-4,5-diyl)bis(diphenylmethanol) ((−)-DDM); and R' is a monodentate achiral ligand selected from the group consisting of alkylalcohols, arylalcohols, arylalkyl alcohols, alkyamines, arylamines, arylalkyl amines, alkylthiols, arylthiols and arylalkyl thiols.

2. The chiral hydride complex of claim 1 selected from the group consisting of:

NaAlH$_2$((+)-DDM);

NaAlH((+)-DDM)(OMe);

NaAlH((+)-DDM)(OEt);

NaAlH((+)-DDM)(OPh);

NaAlH((+)-DDM)(1-NfOH); and

NaAlH((+)-DDM)(OEt-2-OMe).

* * * * *

UNITED STATES PATENT AND TRADEMARK OFFICE
CERTIFICATE OF CORRECTION

PATENT NO. : 6,090,950                    Page 1 of 1
DATED       : July 18, 2000
INVENTOR(S) : Heise, Glenn L.

It is certified that error appears in the above-identified patent and that said Letters Patent is hereby corrected as shown below:

<u>Column 50, claim 1,</u>
Line 4 thereof, "R*" should be -- R** --.

Signed and Sealed this

Twenty-fifth Day of December, 2001

Attest:

JAMES E. ROGAN
*Attesting Officer*          *Director of the United States Patent and Trademark Office*